US010017754B2

(12) United States Patent
Tan et al.

(10) Patent No.: US 10,017,754 B2
(45) Date of Patent: Jul. 10, 2018

(54) GENE ENCODING CELLULASE

(71) Applicant: BASF Enzymes LLC, San Diego, CA (US)

(72) Inventors: Xuqiu Tan, San Diego, CA (US); Kenneth E. Barrett, San Diego, CA (US); Richard S. Lee, San Diego, CA (US)

(73) Assignee: BASF Enzymes LLC, San Diego, CA (US)

( * ) Notice: Subject to any disclaimer, the term of this patent is extended or adjusted under 35 U.S.C. 154(b) by 571 days.

(21) Appl. No.: 14/389,339

(22) PCT Filed: Mar. 12, 2013

(86) PCT No.: PCT/US2013/030527
§ 371 (c)(1),
(2) Date: Sep. 29, 2014

(87) PCT Pub. No.: WO2013/148163
PCT Pub. Date: Oct. 3, 2013

(65) Prior Publication Data
US 2015/0072397 A1 Mar. 12, 2015

Related U.S. Application Data

(60) Provisional application No. 61/618,610, filed on Mar. 30, 2012, provisional application No. 61/704,368, filed on Sep. 21, 2012.

(51) Int. Cl.
C12N 9/42 (2006.01)
C12N 9/24 (2006.01)
C09K 8/52 (2006.01)
C09K 8/68 (2006.01)
C11D 3/386 (2006.01)
C12N 9/26 (2006.01)

(52) U.S. Cl.
CPC .............. C12N 9/2437 (2013.01); C09K 8/52 (2013.01); C09K 8/68 (2013.01); C11D 3/38645 (2013.01); C12N 9/2411 (2013.01); C09K 2208/24 (2013.01)

(58) Field of Classification Search
None
See application file for complete search history.

(56) References Cited

U.S. PATENT DOCUMENTS

| 4,465,598 A | 8/1984 | Darlington et al. |
| 4,536,293 A | 8/1985 | Babineaux, III |
| 4,746,517 A | 5/1988 | Ducroo |
| 4,788,066 A | 11/1988 | Witt |
| 4,896,665 A | 1/1990 | Gervais |
| 5,021,246 A | 6/1991 | Sieben et al. |
| 5,093,008 A | 3/1992 | Clifford, III |
| 5,164,099 A | 11/1992 | Gupta et al. |
| 5,373,901 A | 12/1994 | Norman et al. |
| 5,405,624 A | 4/1995 | Doncheck et al. |
| 5,437,331 A | 8/1995 | Gupta et al. |
| 5,536,650 A | 7/1996 | Versteegh |
| 5,762,991 A | 6/1998 | Dziondziak et al. |
| 6,110,382 A | 8/2000 | Wiemers et al. |
| 6,132,619 A | 10/2000 | Lin et al. |
| 6,163,766 A | 12/2000 | Kleider et al. |
| 6,357,527 B1 | 3/2002 | Norman et al. |
| 6,365,561 B1 | 4/2002 | Vinson et al. |
| 6,380,147 B1 | 4/2002 | Speckmann et al. |
| 6,399,561 B1 | 6/2002 | Schneider et al. |
| 6,413,928 B1 | 7/2002 | Painter et al. |
| 7,323,336 B2 | 1/2008 | Callen et al. |
| 7,754,080 B2 | 7/2010 | Hausin et al. |
| 8,426,184 B2 | 4/2013 | Blum et al. |
| 2005/0130160 A1 | 6/2005 | Chew et al. |
| 2005/0186666 A1 | 8/2005 | Schneider et al. |
| 2008/0058262 A1 | 3/2008 | Rasochova et al. |
| 2008/0233175 A1 | 9/2008 | Steer et al. |
| 2011/0294166 A1 | 12/2011 | Han et al. |

FOREIGN PATENT DOCUMENTS

| CN | 101495644 A | 7/2009 |
| CN | 101528766 A | 9/2009 |
| EP | 2444490 A1 | 4/2012 |
| JP | 61-089202 A | 5/1986 |
| JP | 2009-538622 A | 11/2009 |
| WO | WO 2007/142954 | 12/2007 |
| WO | WO 2009/020459 | 2/2009 |

OTHER PUBLICATIONS

Baker WL, Panow A, "Estimation of cellulase activity using a glucose-oxidase-Cu(II) reducing assay for glucose", J Biochem Biophys Methods. Dec. 1991, 23(4):265-73.
Bibel, M. et al., 1998, "Isolation and analysis of genes for amylolytic enzymes of the hyperthermophilic bacterium *Thermotoga maritima*", FEMS Microbiology Letters, 158:9-15.
Bouthier de la Tour, C. et al., 1998, Reverse Gyrase from the Hyperthermophilic Bacterium *Thermotoga maritima*: Properties and Gene Structure, J. of Bacteriology, 180(2):274-281.
Bronnenmeier, K. et al., (1995), "Purification of Thermotoga maritima enzymes for the degradation of cellulosic materials", Applied and Environmental Microbilogy, 61(4):1399-1407.
Bryant, Rebecca S. et al., Chapter 14, "Microbial Enhanced Oil Recovery", In: Erle C. Donaldson, George V. Chilingarian and Teh Fu Yen, Editor(s), Developments .in Petroleum Science, Elsevier, 1989, vol. 17(B):423-450.
Canevascini G., "A cellulase assay coupled to cellobiose dehydrogenase", Anal Biochem. Jun. 1985, 30 147(2):419-27.
Carder JH, 1986, "Detection and quantitation of cellulase by Congo red staining of substrates in a cupplate diffusion assay", Anal Biochem, 153(1):75-79.

(Continued)

Primary Examiner — Paul J Holland
(74) Attorney, Agent, or Firm — Knobbe Martens Olson & Bear LLP

(57) ABSTRACT

Polynucleotide sequences are provided encoding a thermostable cellulase and directing its increased expression are provided, and the use of the thermostable cellulase in hydraulic fracturing methods and the treatment of flowback fluids.

14 Claims, 19 Drawing Sheets

(56) References Cited

OTHER PUBLICATIONS

Chibata et al., (1986), "Biocatalysis: Immobilized cells and enzymes", J Mol. Cat. 37:1-24.
Geneseq, 2009, GSP:AWI68567, XP-002747767 downloaded Oct. 21, 2015.
Huang JS, Tang J, (1976), "Sensitive assay for cellulase and dextranase", Anal Biochem, 73(2):369-377.
Huber, R. et al., 1986, "*Thermotoga maritima* sp. nov. represents a new genus of unique extremely thermophilic eubacteria growing up to 900C", Arch Microbial, 144:324-333.
Huber, J. et al., 2006, "Microbial life in ridge flank crustal fluids", Environmental Microbiology, 8(1):88-99.
Rogalski, J., 1999, "Immobilization of laccase from *Cerrena unicolor* on controlled porosity glass", J. Mol. Cat. B: Enzymatic 6:29-39.
Karmakar, M. et al., 2011, "Current Trends in Research and Application of Microbial Cellulases", Research Journal of Microbiology, 6(1):41-53.
Liebl, W. et al., 1992, "Purification and characterization of a novel thermostable 4-α-glucanotransferase of Thermotoga maritima cloned in *Escherichia coli*", Eur. J. Biochem, 207:81-88.
Liebl, W. et al., 1994, "Comprative amino acid sequence analysis of Thermotoga maritima β-glucosidase (BglA) deduced from the nucleotide sequence of the gene indicates ditant relationship between β-glucosidases of the BGA family and other families of β-1,4-glycosyl hydrolases", Mol Gen Genet, 242:111-115.
Liebl, W. et al., 1996, an "Analysis of a Thermotoga maritima DNA fragment encoding two similar thermostable cellulases, CelA and CelB, and characterization of the recombinant enzymes", Microbiology, 142:2533-2542.
Liebl, W. et al., 1997, "Properties and Gene Structure of the Thermotoga maritima α-Amylase AmyA, a Putative Lipoprotein of a Hyperthermophilic Bacterium", J. Bacteriology, 179(3):941-948.
Mahadevan et al., (2008), "Site-directed mutagenesis and CBM engineering of Cel5A (*Thermotoga maritima*)", FEMS Microbiology Letters, 287:205-211.
Retallack, Diane et al., (2006), "Pseudomonas fluorescens—a robust expression platform for pharmaceutical protein production", Microbial Cell Factories, 1 pg.
Ruile, P. et al., 1997, "Isolation and analysis of a gene encoding α-gluvuronidase, an enzyme with a novel primary structure involved in the breakdown of xylan", Molecular Microbiology, 23(2):267-279.
Sharma, B. et al., "Immobilized Biomaterials—Techniques and Applications", Angew. Chem. Int. Ed. Engl. 21 (1982) 837-15 54: Laskin (Ed.), Enzymes and Immobilized Cells in Biotechnology.
Sharrock KR, 1988, "Cellulase assay methods: a review", J Biochem Biophys Methods, 17(2):81-106.
Winterhalter, C. et al., 1995, "Two Extremely Thermostable Xylanases of the Hyperthermophilic Bacterium *Thermotoga maritima* MSB8", Applied and Environmental Microbiology, 61(5):1810-1815.
Office Action for Eurasian Patent Application No. 201491586 dated Dec. 30, 2014.
Extended European Search Report for European Patent Application No. 13767815.7 dated Feb. 26, 2016.
International Search Report for International Patent Application No. PCT/US2013/030527 dated Aug. 7, 2013.
International Preliminary Report on Patentability for International Patent Application No. PCT/US2013/030527 dated Oct. 1, 2014.
Office Action with English translation issued by Chinese Patent Office 201380025682.5, dated May 25, 2016.
Japanese Office Action dated Dec. 20, 2016 in Japanese Patent Application No. 2015-503257, filed Sep. 29, 2014.
Office Action dated Feb. 17, 2017, in Chinese Office Action No. CN 201380025682.5 filed Nov. 17, 2014.
Office Action dated Feb. 21, 2018, in Mexican Office Action No. MX/a/2014/011747, filed Sep. 29, 2014.

Legend

Lanes 1, 5, 9 = negative control
Lanes 2, 6, 10 = SEQ ID NO:3
Lane 3, 7, 11 = SEQ ID NO:4
Lane 4, 8, 12 = SEQ ID NO:1
Lane 13 = Molecular Weight Ladder

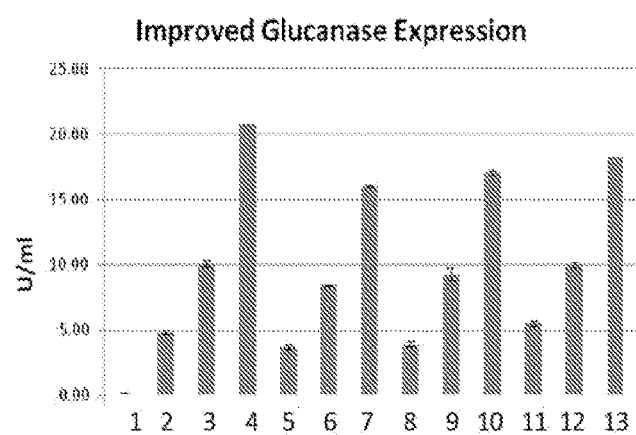
Legend
Lanes 1 = negative control
Lanes 2, 5, 8, 11 = SEQ ID NO:3
Lane 3, 6, 9, 12 = SEQ ID NO:4
Lane 4, 7, 10, 13 = SEQ ID NO:1

Figure 4

SEQ ID NO:1

ATGGGCGTCGATCCGTTTGAACGTAACAAAATCTTGGGCCGCGGCATTAATATCGGC
AATGCGCTCGAAGCACCAAATGAAGGCGACTGGGGAGTGGTGATAAAAGATGAGTTC
TTCGACATTATAAAAGAAGCCGGTTTCTCTCATGTTCGAATTCCAATAAGATGGAGT
ACGCACGCTCAGGCGTTTCCTCCTTATAAAATCGAGCCTTCTTTCTTCAAAAGAGTG
GATGAAGTGATAAACGGAGCCCTGAAAAGAGGACTGGCTGTTGTTATAAATATTCAT
CACTACGAGGAGTTAATGAATGATCCAGAAGAACACAAGGAAAGATTTCTTGCTCTT
TGGAAACAAATTGCTGATCGTTATAAAGACTATCCCGAAACTCTATTTTTTGAAATT
CTGAATGAACCTCACGGAAATCTTACTCCGGAAAAATGGAATGAACTGCTTGAGGAA
GCTCTAAAAGTTATAAGATCAATTGACAAAAAGCACACTGTGATTATAGGCACAGCT
GAATGGGGGGTATATCTGCCCTTGAAAAACTGAGGGTCCCAAAATGGGAAAAAAAT
GCGATAGTTACAATTCACTACTACAATCCTTTCGAATTTACCCATCAAGGAGCTGAG
TGGGTGCCTGGATCTGAGAAATGGTTGGGAAGAAAGTGGGGATCTCCAGATGATCAG
AAACATTTGATAGAAGAATTCAATTTTATAGAAGAATGGTCAAAAAGAACAAAGA
CCAATTTACATAGGTGAGTTTGGTGCCTACAGAAAGCTGACCTTGAATCAAGAATA
AAATGGACCTCCTTTGTCGTTCGCGAAGCCGAGAAAGGGGGTGGAGCTGGGCATAC
TGGGAATTTTGTTCCGGTTTTGGTGTTTATGATCCTCTGAGAAAACAGTGGAATAAA
GATCTTTTAGAAGCTTAATAGGAGGAGATAGCATTGAATGA

Figure 5

SEQ ID NO:2

MGVDPFERNKILGRGINIGNALEAPNEGDWGVVIKDEFFDIIKEAGFSHVRIPIRWS
THAQAFPPYKIEPSFFKRVDEVINGALKRGLAVVINIHHYEELMNDPEEHKERFLAL
WKQIADRYKDYPETLFFEILNEPHGNLTPEKWNELLEEALKVIRSIDKKHTVIIGTA
EWGGISALEKLRVPKWEKNAIVTIHYYNPFEFTHQGAEWVPGSEKWLGRKWGSPDDQ
KHLIEEFNFIEEWSKKNKRPIYIGEFGAYRKADLESRIKWTSFVVREAEKRGWSWAY
WEFCSGFGVYDPLRKQWNKDLLEALIGGDSIE

Figure 6

SEQ ID NO:3

ATGGGTGTTGATCCTTTTGAAAGGAACAAAATATTGGGAAGAGGCATTAATATAGGAAATGCGC
TTGAAGCACCAAATGAGGGAGACTGGGGAGTGGTGATAAAAGATGAGTTCTTCGACATTATAAA
AGAAGCCGGTTTCTCTCATGTTCGAATTCCAATAAGATGGAGTACGCACGCTCAGGCGTTTCCT
CCTTATAAAATCGAGCCTTCTTTCTTCAAAAGAGTGGATGAAGTGATAAACGGAGCCCTGAAAA
GAGGACTGGCTGTTGTTATAAATATTCATCACTACGAGGAGTTAATGAATGATCCAGAAGAACA
CAAGGAAAGATTTCTTGCTCTTTGGAAACAAATTGCTGATCGTTATAAAGACTATCCCGAAACT
CTATTTTTTGAAATTCTGAATGAACCTCACGGAAATCTTACTCCGGAAAAATGGAATGAACTGC
TTGAGGAAGCTCTAAAAGTTATAAGATCAATTGACAAAAAGCACACTGTGATTATAGGCACAGC
TGAATGGGGGGTATATCTGCCCTTGAAAAACTGAGGGTCCCAAAATGGGAAAAAAATGCGATA
GTTACAATTCACTACTACAATCCTTTCGAATTTACCCATCAAGGAGCTGAGTGGGTGCCTGGAT
CTGAGAAATGGTTGGGAAGAAAGTGGGATCTCCAGATGATCAGAAACATTTGATAGAAGAATT
CAATTTTATAGAAGAATGGTCAAAAAAGAACAAAAGACCAATTTACATAGGTGAGTTTGGTGCC
TACAGAAAAGCTGACCTTGAATCAAGAATAAAATGGACCTCCTTTGTCGTTCGCGAAGCCGAGA
AAAGGGGTGGAGCTGGGCATACTGGGAATTTTGTTCCGGTTTTGGTGTTATGATCCTCTGAG
AAAACAGTGGAATAAAGATCTTTTAGAAGCTTTAATAGGAGGAGATAGCATTGAATAA

Figure 7

SEQ ID NO:4

```
TCTACTAGTTAGGAGGTAACTTATGGGCGTCGATCCGTTTGAACGTAACAAAATCTTGGGCCGC
GGCATTAATATCGGCAATGCGCTCGAAGCACCAAATGAAGGCGACTGGGGAGTGGTGATAAAAG
ATGAGTTCTTCGACATTATAAAAGAAGCCGGTTTCTCTCATGTTCGAATTCCAATAAGATGGAG
TACGCACGCTCAGGCGTTTCCTCCTTATAAAATCGAGCCTTCTTTCTTCAAAAGAGTGGATGAA
GTGATAAACGGAGCCCTGAAAAGAGGACTGGCTGTTGTTATAAATATTCATCACTACGAGGAGT
TAATGAATGATCCAGAAGAACACAAGGAAAGATTTCTTGCTCTTTGGAAACAAATTGCTGATCG
TTATAAAGACTATCCCGAAACTCTATTTTTTGAAATTCTGAATGAACCTCACGGAAATCTTACT
CCGGAAAAATGGAATGAACTGCTTGAGGAAGCTCTAAAAGTTATAAGATCAATTGACAAAAAGC
ACACTGTGATTATAGGCACAGCTGAATGGGGGGGTATATCTGCCCTTGAAAAACTGAGGGTCCC
AAAATGGGAAAAAAATGCGATAGTTACAATTCACTACTACAATCCTTTCGAATTTACCCATCAA
GGAGCTGAGTGGGTGCCTGGATCTGAGAAATGGTTGGGAAGAAAGTGGGGATCTCCAGATGATC
AGAAACATTTGATAGAAGAATTCAATTTTATAGAAGAATGGTCAAAAAAGAACAAAAGACCAAT
TTACATAGGTGAGTTTGGTGCCTACAGAAAAGCTGACCTTGAATCAAGAATAAAATGGACCTCC
TTTGTCGTTCGCGAAGCCGAGAAAAGGGGGTGGAGCTGGGCATACTGGGAATTTTGTTCCGGTT
TTGGTGTTTATGATCCTCTGAGAAAACAGTGGAATAAAGATCTTTTAGAAGCTTTAATAGGAGG
AGATAGCATTGAATGA
```

Figure 8

SEQ ID NO:5

ATGGGTGTTGATCCTTTTGAAAGGAACAAAATATTGGGAAGAGGCATTAATATAGGAAATGCGC
TTGAAGCACCAAATGAGGGAGACTGGGGAGTGGTGATAAAAGATGAGTTCTTCGACATTATAAA
AGAAGCCGGTTTCTCTCATGTTCGAATTCCAATAAGATGGAGTACGCACGCTTACGCGTTTCCT
CCTTATAAAATCATGGATCGCTTCTTCAAAAGAGTGGATGAAGTGATAAACGGAGCCCTGAAAA
GAGGACTGGCTGTTGTTATAAATATTCATCACTACGAGGAGTTAATGAATGATCCAGAAGAACA
CAAGGAAAGATTTCTTGCTCTTTGGAAACAAATTGCTGATCGTTATAAAGACTATCCCGAAACT
CTATTTTTTGAAATTCTGAATGAACCTCACGGAAATCTTACTCCGGAAAAATGGAATGAACTGC
TTGAGGAAGCTCTAAAAGTTATAAGATCAATTGACAAAAGCACACTATAATTATAGGCACAGC
TGAATGGGGGGGTATATCTGCCCTTGAAAAACTGTCTGTCCCAAAATGGGAAAAAAATTCTATA
GTTACAATTCACTACTACAATCCTTTCGAATTTACCCATCAAGGAGCTGAGTGGGTGGAAGGAT
CTGAGAAATGGTTGGGAAGAAAGTGGGGATCTCCAGATGATCAGAAACATTTGATAGAAGAATT
CAATTTTATAGAAGAATGGTCAAAAAAGAACAAAAGACCAATTTACATAGGTGAGTTGGTGCC
TACAGAAAAGCTGACCTTGAATCAAGAATAAAATGGACCTCCTTTGTCGTTCGCGAAATGGAGA
AAGGAGATGGAGCTGGGCATACTGGGAATTTTGTTCCGGTTTTGGTGTTTATGATACTCTGAG
AAAAACCTGGAATAAAGATCTTTTAGAAGCTTTAATAGGAGGAGATAGCATTGAATAA

Figure 9

SEQ ID NO:6

MGVDPFERNKILGRGINIGNALEAPNEGDWGVVIKDEFFDIIKEAGFSHVRIPIRWSTHAYAFP
PYKIMDRFFKRVDEVINGALKRGLAVVINIHHYEELMNDPEEHKERFLALWKQIADRYKDYPET
LFFEILNEPHGNLTPEKWNELLEEALKVIRSIDKKHTIIIGTAEWGGISALEKLSVPKWEKNSI
VTIHYYNPFEFTHQGAEWVEGSEKWLGRKWGSPDDQKHLIEEFNFIEEWSKKNKRPIYIGEFGA
YRKADLESRIKWTSFVVREMEKRRWSWAYWEFCSGFGVYDTLRKTWNKDLLEALIGGDSIE

Figure 10

SEQ ID NO:7

ATGGAACAGTCAGTTGCTGAAAGTGATAGCAACTCAGCATTTGAATACAACAAAATGGTAGGTA
AAGGAGTAAATATTGGAAATGCTTTAGAAGCTCCTTTCGAAGGAGCTTGGGGAGTAAGAATTGA
GGATGAATATTTTGAGATAATAAAGAAAAGGGGATTTGATTCTGTTAGGATTCCCATAAGATGG
TCAGCACATATATCCGAAAAGCCACCATATGATATTGACAGGAATTTCCTCGAAAGAGTTAACC
ATGTTGTCGATAGGGCTCTTGAGAATAATTTAACAGTAATCATCAATACGCACCATTTTGAAGA
ACTCTATCAAGAACCGGATAAATACGGCGATGTTTTGGTGGAAATTTGGAGACAGATTGCAAAA
TTCTTTAAAGATTACCCGGAAAATCTGTTCTTTGAAATCTACAACGAGCCTGCTCAGAACTTGA
CAGCTGAAAAATGGAACGCACTTTATCCAAAAGTGCTCAAAGTTATCAGGGAGAGCAATCCAAC
CCGGATTGTCATTATCGATGCTCCAAACTGGGCACACTATAGCGCAGTGAGAAGTCTAAAATTA
GTCAACGACAAACGCATCATTGTTTCCTTCCATTACTACGAACCTTTCAAATTCACACATCAGG
GTGCCGAATGGGTTAATCCCATCCCACCTGTTAGGGTTAAGTGGAATGGCGAGGAATGGGAAAT
TAACCAAATCAGAAGTCATTTCAAATACGTGAGTGACTGGGCAAAGCAAAATAACGTACCAATC
TTTCTTGGTGAATTCGGTGCTTATTCAAAAGCAGACATGGACTCAAGGGTTAAGTGGACCGAAA
GTGTGAGAAAAATGGCGGAAGAATTTGGATTTTCATACGCGTATTGGGAATTTTGTGCAGGATT
TGGCATATACGATAGATGGTCTCAAAACTGGATCGAACCATTGGCAACAGCTGTGGTTGGCACA
GGCAAAGAGTAA

Figure 11

SEQ ID NO:8

MEQSVAESDSNSAFEYNKMVGKGVNIGNALEAPFEGAWGVRIEDEYFEIIKKRGFDSVRIPIRW
SAHISEKPPYDIDRNFLERVNHVVDRALENNLTVIINTHHFEELYQEPDKYGDVLVEIWRQIAK
FFKDYPENLFFEIYNEPAQNLTAEKWNALYPKVLKVIRESNPTRIVIIDAPNWAHYSAVRSLKL
VNDKRIIVSFHYYEPFKFTHQGAEWVNPIPPVRVKWNGEEWEINQIRSHFKYVSDWAKQNNVPI
FLGEFGAYSKADMDSRVKWTESVRKMAEEFGFSYAYWEFCAGFGIYDRWSQNWIEPLATAVVGT
GKE

Figure 12

SEQ ID NO:9

ATGGGTGTTGATCCTTTTGAAAGGAACAAAATATTGGGAAGAGGCATTAATATAGGAAATGCGC
TTGAAGCACCAAATGAGGGAGACTGGGGAGTGGTGATAAAAGATGAGTATTTCGACATTATAAA
AGAAGCCGGTTTCTCTCATGTTCGAATTCCAATAAGATGGAGTACGCACGCTCAGGCGTTTCCT
CCTTATAAAATCGAGGATCGCTTCTTCAAAAGAGTGGATGAAGTGATAAACGGAGCCCTGAAAA
GAGGACTGGCTGTTGTTATAAATCAGCATCACTACGAGGAGTTAATGAATGATCCAGAAGAACA
CAAGGAAAGATTTCTTGCTCTTTGGAAACAAATGCTGATCGTTATAAAGACTATCCCGAAACT
CTATTTTTTGAAATTCTGAATGAACCTCACGGAAATCTTACTCCGGAAAAATGGAATGAACTGC
TTGAGGAAGCTCTAAAAGTTATAAGATCAATTGACAAAAAGCACACTATAATTATAGGCACAGC
TGAATGGGGGGTATATCTGCCCTTGAAAAACTGAGGGTCCCAAAATGGGAAAAAAATGCGATA
GTTACAATTCACTACTACAATCCTTTCGAATTTACCCATCAAGGAGCTGAGTGGGTGGAAGGAT
CTGAGAAATGGTTGGGAAGAAAGTGGGGATCTCCAGATGATCAGAAACATTTGATAGAAGAATT
CAATTTTATAGAAGAATGGTCAAAAAAGAACAAAAGACCAATTTACATAGGTGAGTTTGGTGCC
TACAGAAAAGCTGACCTTGAATCAAGAATAAAATGGACCTCCTTGTCGTTCGCGAAGCTGAGA
AAAGGAGATGGAGCTGGGCATACTGGGAATTTTGTTCCGGTTTTGGTGTTTATGATACTCTGAG
AAAAACCTGGAATAAAGATCTTTTAGAAGCTTTAATAGGAGGAGATAGCATTGAATAACACCAT
TCCAAGATGGCGTG

Figure 13

SEQ ID NO:10

MGVDPFERNKILGRGINIGNALEAPNEGDWGVVIKDEYFDIIKEAGFSHVRIPIRWSTHAQAFP
PYKIEDRFFKRVDEVINGALKRGLAVVINQHHYEELMNDPEEHKERFLALWKQIADRYKDYPET
LFFEILNEPHGNLTPEKWNELLEEALKVIRSIDKKHTIIIGTAEWGGISALEKLRVPKWEKNAI
VTIHYYNPFEFTHQGAEWVEGSEKWLGRKWGSPDDQKHLIEEFNFIEEWSKKNKRPIYIGEFGA
YRKADLESRIKWTSFVVREAEKRRWSWAYWEFCSGFGVYDTLRKTWNKDLLEALIGGDSIEHHS
KMA

Figure 14

SEQ ID NO:11

ATGGGTGTTGATCCTTTTGAAAGGAACAAAATATTGGGAAGAGGCATTAATATAGGAAATGCGC
TTGAAGCACCAAATGAGGGAGACTGGGGAGTGGTGATAAAAGATGAGTATTTCGACATTATAAA
AGAAGCCGGTTTCTCTCATGTTCGAATTCCAATAAGATGGAGTACGCACGCTCAGGCGTTTCCT
CCTTATAAAATCGAGGATTCTTTCTTCAAAAGAGTGGATGAAGTGATAAACGGAGCCCTGAAAA
GAGGACTGGCTGTTGTTATAAATATTCATCACTACGAGGAGTTAATGAATGATCCAGAAGAACA
CAAGGAAAGATTTCTTGCTCTTTGGAAACAAATGCTGATCGTTATAAAGACTATCCCGAAACT
CTATTTTTTGAAATTCTGAATGAACCTCACGGAAATCTTACTCCGGAAAAATGGAATGAACTGC
TTGAGGAAGCTCTAAAAGTTATAAGATCAATTGACAAAAAGCACACTGTGATTATAGGCACAGC
TGAATGGGGGGGTATATCTGCCCTTGAAAAACTGAGGGTCCCAAAATGGGAAAAAAATGCGATA
GTTACAATTCACTACTACAATCCTTTCGAATTTACCCATCAAGGAGCTGAGTGGGTGCCTGGAT
CTGAGAAATGGTTGGGAAGAAAGTGGGGATCTCCAGATGATCAGAAACATGTGATAGAAGAATT
CAATTTTATAGAAGAATGGTCAAAAAAGAACAAAAGACCAATTTACATAGGTGAGTTTGGTGCC
TACAGAAAAGCTGACCTTGAATCAAGAATAAAATGGACCTCCTTTGTCGTTCGCGAAGCCGAGA
AAAGGGGGTGGAGCTGGGCATACTGGGAATTTTGTTCCGGTTTTGGTGTTTATGATCCTCTGAG
AAAACAGTGGAATAAAGATCTTTTAGAAGCTCTAATAGGAGGAGATAGCATTGAATAA

Figure 15

SEQ ID NO:12

MGVDPFERNKILGRGINIGNALEAPNEGDWGVVIKDEYFDIIKEAGFSHVRIPIRWSTHAQAFP
PYKIEDSFFKRVDEVINGALKRGLAVVINIHHYEELMNDPEEHKERFLALWKQIADRYKDYPET
LFFEILNEPHGNLTPEKWNELLEEALKVIRSIDKKHTVIIGTAEWGGISALEKLRVPKWEKNAI
VTIHYYNPFEFTHQGAEWVPGSEKWLGRKWGSPDDQKHVIEEFNFIEEWSKKNKRPIYIGEFGA
YRKADLESRIKWTSFVVREAEKRGWSWAYWEFCSGFGVYDPLRKQWNKDLLEALIGGDSIE

Figure 16

SEQ ID NO:13

ATGGGTGTTGATCCTTTTGAAAGGAACAAAATATTGGGAAGAGGCATTAATATAGGAAATGCGC
TTGAAGCACCAAATGAGGGAGACTGGGGAGTGGTGATAAAAGATGAGTTCTTCGACATTATAAA
AGAAGCCGGTTTCTCTCATGTTCGAATTCCAATAAGATGGAGTACGCACGCTCAGGCGTTTCCT
CCTTATAAAATCGAGGATTCTTTCTTCAAAAGAGTGGATGAAGTGATAAACGGAGCCCTGAAAA
GAGGACTGGCTGTTGTTATAAATCAGCATCACTACGAGGAGTTAATGAATGATCCAGAAGAACA
CAAGGAAAGATTTCTTGCTCTTTGGAAACAAATTGCTGATCGTTATAAAGACTATCCCGAAACT
CTATTTTTTGAAATTCTGAATGAACCTCACGGAAATCTTACTCCGGAAAAATGGAATGAACTGC
TTGAGGAAGCTCTAAAAGTTATAAGATCAATTGACAAAAGCACACTGTGATTATAGGCACAGC
TGAATGGGGGGGTATATCTGCCCTTGAAAAACTGAGGGTCCCAAAATGGGAAAAAAATGCGATA
GTTACAATTCACTACTACAATCCTTTCGAATTTACCCATCAAGGAGCTGAGTGGGTGCCTGGAT
CTGAGAAATGGTTGGGAAGAAAGTGGGGATCTCCAGATGATCAGAAACATTTGATAGAAGAATT
CAATTTTATAGAAGAATGGTCAAAAAAGAACAAAAGACCAATTTACATAGGTGAGTTTGGTGCC
TACAGAAAAGCTGACCTTGAATCAAGAATAAAATGGACCTCCTTTGTCGTTCGCGAAGCCGAGA
AAAGGGGTGGAGCTGGGCATACTGGGAATTTTGTTCCGGTTTTGGTGTTTATGATCCTCTGAG
AAAACAGTGGAATAAAGATCTTTTAGAAGCTTTAATAGGAGGAGATAGCATTGAATAA

Figure 17

SEQ ID NO:14

MGVDPFERNKILGRGINIGNALEAPNEGDWGVVIKDEFFDIIKEAGFSHVRIPIRWSTHAQAFP
PYKIEDSFFKRVDEVINGALKRGLAVVINQHHYEELMNDPEEHKERFLALWKQIADRYKDYPET
LFFEILNEPHGNLTPEKWNELLEEALKVIRSIDKKHTVIIGTAEWGGISALEKLRVPKWEKNAI
VTIHYYNPFEFTHQGAEWVPGSEKWLGRKWGSPDDQKHLIEEFNFIEEWSKKNKRPIYIGEFGA
YRKADLESRIKWTSFVVRRAEKRGWSWAYWEFCSGFGVYDPLRKQWNKDLLEALIGGDSIE

Figure 18

SEQ ID NO:15

ATGGCCAAGTACTCCGAGCTGGAAAAGGGCGGGGTCATAATGCAGGCGTTCTACTGGGACGTGC
CTTCAGGAGGAATATGGTGGGACACAATACGGCAGAAGATACCGGAGTGGTACGATGCCGGAAT
CTCCGCAATATGGATTCCCCCGGCGAGCAAGGGCATGGGCGGCGCCTATTCGATGGGCTACGAC
CCCTACGACTTCTTTGACCTCGTGAGTACGACCAGAAGGGAACGGTAGAGACGCGCTTTGGCTC
CAAGCAGGAGCTCGTGAACATGATAAACACCGCCCACGCCTATGGCATGAAGGTAATAGCCGAT
ATAGTCATCAACCACCGCGCCGGCGGTGACCTGGAGTGGAACCCCTTCGTGAACGACTATACCT
GGACCGACTTCTCAAAGGTCGCGTCGGGTAAATACACGGCCAACTACCTCGACTTCCACCCGAA
CGAGCTCCATGCGGGCGATTCCGGGACATTTGGAGGCTATCCCGACATATGCCACGACAAGAGC
TGGGACCAGTACTGGCTCTGGGCCAGCCAGGAGAGCTACGCGGCATATCTCAGGAGCATCGGCA
TCGATGCCTGGCGCTTCGACTACGTCAAGGGCTATGCTCCCTGGGTCGTCAAGGACTGGCTGAA
CTGGTGGGGAGGCTGGGCGGTTGGAGAGTACTGGGACACCAACGTCGACGCTGTTCTCAACTGG
GCATACTCGAGCGGTGCCAAGGTCTTTGACTTCGCCCTCTACTACAAGATGGATGAGGCCTTTG
ACAACAAAAACATTCCAGCGCTCGTCTCTGCCCTTCAGAACGGCCAGACTGTTGTCTCCCGCGA
CCCGTTCAAGGCCGTAACCTTTGTAGCAAACCACGACACCGATATAATCTGGAACAAGTATCCA
GCCTACGCGTTCATCCTCACCTACGAGGGCCAGCCGACAATATTCTACCGCGACTACGAGGAGT
GGCTCAACAAGGATAAGCTCAAGAACCTCATCTGGATACATGAGAACCTCGCCGGAGGAAGCAC
CGACATAGTCTACTACGATAACGATGAACTCATCTTCGTCAGGAACGGCTACGGGGACAAGCCG
GGGCTTATAACCTACATCAACCTAGGCTCGAGCAAGGCCGGAAGGTGGGTTTATGTGCCGAAGT
TCGCGGGCGCGTGCATCCACGAGTATACTGGTAACCTCGGAGGCTGGGTAGACAAGTACGTCTA
CTCAAGCGGCTGGGTCTATCTCGAAGCTCCAGCTTACGACCCTGCCAACGGGCAGTATGGCTAC
TCCGTGTGGAGCTACTGCGGGGTGGGCTGA

Figure 19

SEQ ID NO:16

```
MAKYSELEKGGVIMQAFYWDVPSGGIWWDTIRQKIPEWYDAGISAIWIPPASKGMGGAYSMGYD
PYDFFDLGEYDQKGTVETRFGSKQELVNMINTAHAYGMKVIADIVINHRAGGDLEWNPFVNDYT
WTDFSKVASGKYTANYLDFHPNELHAGDSGTFGGYPDICHDKSWDQYWLWASQESYAAYLRSIG
IDAWRFDYVKGYAPWVVKDWLNWWGGWAVGEYWDTNVDAVLNWAYSSGAKVFDFALYYKMDEAF
DNKNIPALVSALQNGQTVVSRDPFKAVTFVANHDTDIIWNKYPAYAFILTYEGQPTIFYRDYEE
WLNKDKLKNLIWIHENLAGGSTDIVYYDNDELIFVRNGYGDKPGLITYINLGSSKAGRWVYVPK
FAGACIHEYTGNLGGWVDKYVYSSGWVYLEAPAYDPANGQYGYSVWSYCGVG
```

GENE ENCODING CELLULASE

RELATED APPLICATIONS

This application is a U.S. National Phase Application of PCT International Application Number PCT/US2013/030527, filed on Mar. 12, 2013, designating the United States of America and published in the English language, which is an International Application of and claims the benefit of priority to U.S. Provisional Applications 61/618,610, filed on Mar. 30, 2012 and 61/704,368, filed on Sep. 21, 2012. The disclosures of the above-referenced applications are herein expressly incorporated by reference in their entireties.

FIELD OF THE INVENTION

Polynucleotide sequences encoding a cellulase are provided. In particular, the polynucleotide sequences may provide increased expression of a specific, thermostable, thermotolerant, pressure stable enzyme such as a cellulase.

SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is SeqList_$_{VEREN}$2_001NP.txt, the date of creation of the ASCII text file is Sep. 29, 2014, and the size of the ASCII text file is 31.5 KB.

BACKGROUND OF THE INVENTION

O-Glycosyl hydrolases (EC 3.2.1.-) are a widespread group of naturally-occurring enzymes that hydrolyze the glycosidic bond between two or more carbohydrates or between a carbohydrate and a non-carbohydrate moiety. The International Union of Biochemistry and Molecular Biology (IUBMB) enzyme nomenclature of glycosyl hydrolases (or glycosylases) is based principally on their substrate specificity and occasionally on their molecular mechanism (Nomenclature Committee of the International Union of Biochemistry and Molecular Biology (NC-IUBMB), Accessed Oct. 24, 2011).

IUBMB Enzyme Nomenclature EC 3.2.1.4 has been designated for a subgroup group of glycosylase-type enzymes termed "cellulases." Other names used for enzymes belonging to this group include: endoglucanase, endo-1,4-beta-glucanase, carboxymethyl cellulase, and beta-1,4-glucanase. The reaction catalyzed by enzymes belonging to this group is the endo-hydrolysis of 1,4-beta-D-glycosidic linkages in cellulose, lichenin, and cereal beta-D-glucans (such as barley beta-glucan). Since the predominant activities of the disclosed cellulase of the present invention are the endo-hydrolysis of barley beta-glucan and carboxymethyl cellulose, it is appropriately ascribed the IUBMB Enzyme Nomenclature EC 3.2.1.4.

An alternative classification of glycosyl hydrolases is based on amino acid sequence similarities (Henrissat, B. Accessed at UniProt Oct. 26, 2011). According to this classification scheme, glycosyl hydrolases can be divided into more than 70 families. Based on a comparison of the primary amino acid sequence of the disclosed cellulase of the present invention with the sequences of other glycosyl hydrolases contained in public databases, the disclosed cellulase of the present invention may be assigned to glycosyl hydrolase Family 5. This family contains more than 20 endoglucanases (IUBMB Enzyme Nomenclature EC 3.2.1.4) whose predominant catalytic activity is the endo-hydrolysis of beta-1,4-glycosidic linkages in cellulosic substrates. Using this second way of classifying enzymes provides further support for the conclusion that the disclosed cellulase of the present invention should be ascribed the IUBMB Enzyme Nomenclature EC 3.2.1.4.

Cellulases are used for a variety of industrial and commercial purposes including but not limited to oil and gas exploration, food and beverage, alcohol production potable or fuel, e.g. brewing, ethanol, wine, flavor, fragrance, textile, detergents, paper, pulp, environmental, and agriculture, as well as in research purposes. (Rebecca S. Bryant, Erie C. Donaldson, Teh Fu Yen, George V. Chilingarian, Chapter 14 Microbial Enhanced Oil Recovery, In: Erle C. Donaldson, George V. Chilingarian and Teh Fu Yen, Editor(s), *Developments in Petroleum Science*, Elsevier, 1989, Volume 17(B):423-450) (M. Karmakar and R. R. Ray, 2011. Current Trends in Research and Application of Microbial Cellulases. *Research Journal of Microbiology*, 6:41-53.).

A typical corollary activity and expense to oil and gas discovery and drilling operations is the treatment of fluids used and or produced by such operations. For example, the drilling of wells, the washing and prepping of wells ("well completion"), hydraulic fracturing operations, and oil and gas processing, all typically produce thousands of gallons of a contaminated by-product fluid. Often the by-product fluids created by such operations are called "flowback fluids," as the liquids typically flow back out of the wellbore to the surface. The by-product fluid, or flowback, must typically be treated for either disposal or reuse.

Need for more efficient means to treat flowback fluids

As the treatment of flowback fluids in the gas discovery and drilling industry requires considerable resources and time, a need exists for efficient methods or compositions to treat flowback fluid. Additionally, as gas discovery and drilling operations typically require fresh (e.g. cleaned or filtered) fluids, a significant need exists for methods to treat flowback fluids to allow the re-use of such fluids for additional gas discovery and drilling operations.

SUMMARY

Enzymes are proteins that act as catalysts. Proteins are polymers of amino acids linked in dehydration reactions by peptide bonds. The identity of the amino acids and the order in which they are linked to form proteins determines a given protein's activity. This order in which amino acids are assembled into proteins (the protein "sequence") is ultimately determined by the sequence of a DNA strand which "encodes" the protein.

The three-nucleotide sequence that specifies a given amino acid to be assembled into a protein is called a "codon." The 20 amino acids built into proteins are collectively encoded by 64 tri-nucleotide codon sequences. The series of codons which specifies a protein is called an "Open Reading Frame." An amino acid may be specified by as few as one or as many as six distinct codons. A change (or mutation) in the trinucleotide sequence of a codon that does not affect the amino acid specified is called a "silent" mutation.

As a result, there are many DNA sequences capable of encoding the same protein, because the DNA sequences differ from one another only through "silent" mutations. By altering one or more of the codons which encode a given protein, it may be possible to greatly increase the amount of protein which a gene produces without affecting the sequence of the protein that is encoded.

In some embodiments, the invention comprises SEQ ID NO:1. In some embodiments, the invention comprises the polynucleotide sequence of SEQ ID NO: 1. In some embodiments, this sequence encodes a protein. In some embodiments, this protein is an enzyme having cellulase activity.

The improved nucleotide sequence disclosed herein is given as SEQ ID NO:1 and encodes a previously disclosed cellulase enzyme (SEQ ID NO:2) that was evolved from a parent cellulase enzyme isolated from a DNA library originating from *Thermotoga maritima* strain MSB8. The disclosed cellulase of SEQ ID NO:2 is described in PCT Publication No. WO 2009/020459, as SEQ ID NO:9 of that reference (encoded by the polynucleotide SEQ ID NO:8 of the same publication, described herein as SEQ ID NO:3). In some embodiments, the invention comprises the polynucleotide sequence of SEQ ID NO:1, or fragments thereof. In some embodiments, these sequences encode a protein. In some embodiments, the protein is an enzyme having cellulase activity.

The invention comprises multiple nucleotide base changes with respect to SEQ ID NO:3. These changes are silent as to the encoded protein. The 14 base changes are set forth below. "Position" indicates the number of the nucleotide within the Open Reading Frame of SEQ ID NO:1, with the first nucleotide of the first codon numbered as 1. In the event that the Open Reading Frame of SEQ ID NO:1 is joined to another nucleic acid sequence at its 5' end so that the Open Reading Frame extends beyond the 5' end of SEQ ID NO:1, the "Position" will continue to refer to the bases as numbered from the 5' end of the Open Reading Frame of SEQ ID NO:1. Similarly, if the Open Reading Frame of SEQ ID NO:1 is truncated so that the Open Reading Frame does not begin at the 5' end of a sequence related to SEQ ID NO:1, the numbering system will continue to originate from the 5' end of said sequence corresponding to the 5' end of SEQ ID NO:1.

The nucleotide base changes, or mutations, are specified using the notation "(old nucleotide) (position) (new nucleotide)." The mutations are as follows: T6C, T9C, T15G, A22C, G24T, A33C, A39C, A40C, A42C, A54C, A57C, T66C, G81A, A84C, and can be found alone or in any combination thereof up to and including all of the above base changes in a single sequence.

The base changes which distinguish SEQ ID NO:1 from prior reported sequences encoding the disclosed cellulase, collectively and individually, result in an Open Reading Frame which leads to a higher level of protein expression than previously employed nucleotide sequences encoding the same protein.

In some embodiments, a nucleotide sequence encoding a cellulase derived from *Thermotoga maritima* is disclosed, wherein the nucleotide sequence comprises at least one mutation selected from T6C, T9C, T15G, A22C, G24T, A33C, A39C, A40C, A42C, A54C, A57C, T66C, G81A, A84C, A6C, G6C, A9C, G9C, A15G, C15G, T22C, G22C, A24T, C24T, T33C, G33C, T39C, G39C, T40C, G40C, T42C, G42C, T54C, G54C, T57C, G57C, A66C, G66C, C81A, T81A, T84C, G84C, or any combination thereof up to and including all of the above base changes in a single sequence. In some aspects of these embodiments, at least one mutation is silent as to the sequence of the encoded protein. In other aspects, at least one mutation results in the nucleotide sequence harboring at least one mutation directing expression of the cellulase at a higher level than a nucleotide sequence lacking at least one mutation and not otherwise differing from the nucleotide sequence of above.

In some embodiments, a nucleotide sequence encoding a cellulase is disclosed, wherein the nucleotide sequence comprises SEQ ID NO:3 and has at least one mutation selected from T6C, T9C, T15G, A22C, G24T, A33C, A39C, A40C, A42C, A54C, A57C, T66C, G81A, A84C, A6C, G6C, A9C, G9C, A15G, C15G T22C, G22C, A24T, C24T, T33C, G33C, T39C, G39C, T40C, G40C, T42C, G42C, T54C, G54C, T57C, G57C, A66C, G66C, C81A, T81A, T84C, G84C, or any combination thereof up to and including all of the above base changes in a single sequence.

In some embodiments, a nucleotide sequence from *Thermotoga maritima* is disclosed having at least one mutation which increases the expression level of a protein encoded by said nucleotide sequence compared to a *Thermotoga maritima* genomic sequence. In some aspects, at least one mutation is silent.

In some embodiments, a first nucleotide sequence encoding the polypeptide of SEQ ID NO:2 is disclosed wherein the nucleotide sequence has been mutated with respect to a second sequence encoding the polypeptide of SEQ ID NO:2 such that the expression level of the protein is increased relative to that of the protein encoded by the second nucleotide sequence.

The invention provides compositions and methods for the treatment of flowback fluids produced in the oil and gas discovery and drilling operations. In some aspects, the composition and methods disclosed herein are used to treat flowback fluids to allow proper environment disposal. In some aspects, the composition and methods disclosed herein are used to treat flowback fluids for further use in oil and gas discovery and drilling operations, or in other words, to recycle the flowback fluids.

In some embodiments, enzymes are used to practice this invention, including any amylase and/or cellulase such as the enzyme disclosed in SEQ ID NO:2, for example, which includes using "cocktails" of enzymes described herein, and/or other enzymes.

In some embodiments, the invention provides for the addition of an amylase, and/or cellulase, such as the enzyme disclosed in SEQ ID NO:2, for example, in the flowback fluid produced in the oil and gas discovery and drilling operations.

Alternative embodiments include an amylases and/or cellulase, e.g., as described herein:

The compositions and methods disclosed herein comprise use of isolated, synthetic or recombinant nucleic acids comprising a nucleic acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary nucleic acid used to practice the invention, including SEQ ID NO:1, SEQ ID NO:5, SEQ ID NO:7, SEQ ID NO:9, SEQ ID NO:11, SEQ ID NO:13, and/or SEQ ID NO:15 over a region of at least about 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, or more residues, wherein these nucleic acids encode at least one polypeptide having a cellulase activity in particular, the genus based on the exemplary SEQ ID NO:2, SEQ ID NO:6, SEQ ID NO:8, SEQ ID NO:10, SEQ ID NO:12, SEQ ID NO:14 and/or at least one polypeptide having amylase activity in particular, the genus based on the exemplary SEQ ID NO:16.

The compositions and methods disclosed herein comprise use of isolated, synthetic, or recombinant polypeptides having a cellulase activity in particular, the genus based on the exemplary ID NO:2, SEQ ID NO:6, SEQ ID NO:8, SEQ ID NO:10, SEQ ID NO:12, and/or SEQ ID NO:14, and/or amylase activity in particular, the genus based on the exemplary SEQ ID NO:16.

In some aspects, the polypeptides used to practice this invention have an amylase or cellulase activity, which is thermostable. The polypeptide can retain an amylase or cellulase activity under conditions comprising a temperature range from about −100° C. to about −80° C., about −80° C. to about −60° C., about −60° C. to about −40° C., about −80° C. to about −40° C., about −40° C. to about −20° C., about −20° C. to about 0° C., about 0° C. to about 37° C., about 0° C. to about 5° C., about 5° C. to about 15° C., about 15° C. to about 25° C., about 25° C. to about 37° C., about 37° C. to about 45° C., about 45° C. to about 55° C., about 55° C. to about 70° C., about 70° C. to about 75° C., about 75° C. to about 85° C., about 85° C. to about 90° C., about 90° C. to about 95° C., about 95° C. to about 100° C., about 100° C. to about 105° C., about 105° C. to about 110° C., about 110° C. to about 120° C., or 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C., 116° C., 117° C., 118° C., 119° C., 120° C., 121° C., 122° C., 123° C., 124° C., 125° C., or more. The polypeptide can retain an amylase or cellulose activity in temperatures in the range between about −100° C. to about −80° C., about −80° C. to about −40° C., about −80° C. to about −60° C., about −60° C. to about −40° C., about −40° C. to about −20° C., about −20° C. to about 0° C., about 0° C. to about 5° C., about 5° C. to about 15° C., about 15° C. to about 25° C., about 25° C. to about 37° C., about 37° C. to about 45° C., about 45° C. to about 55° C., about 55° C. to about 70° C., about 70° C. to about 75° C., about 75° C. to about 85° C., about 85° C. to about 90° C., about 90° C. to about 95° C., about 95° C. to about 100° C., about 100° C. to about 105° C., about 105° C. to about 110° C., about 110° C. to about 120° C., or 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C., 116° C., 117° C., 118° C., 119° C., 120° C., 121° C., 122° C., 123° C., 124° C., 125° C. or more.

In some aspects, the polypeptides used to practice this invention have an amylase, or cellulase activity, which is thermotolerant. The polypeptides can retain an amylase, or a cellulase activity after exposure to a temperature in the range from greater than 37° C. to about 95° C. or anywhere in the range from greater than 55° C. to about 85° C. The polypeptide can retain an amylase, or cellulase activity after exposure to a temperature in the range between about −100° C. to about −80° C., about −80° C. to about −40° C., about −80° C. to about −60° C., about −60° C. to about −40° C., about −40° C. to about −20° C., about −20° C. to about 0° C., about 0° C. to about 5° C., about 5° C. to about 15° C., about 15° C. to about 25° C., about 25° C. to about 37° C., about 37° C. to about 45° C., about 45° C. to about 55° C., about 55° C. to about 70° C., about 70° C. to about 75° C., about 75° C. to about 85° C., about 85° C. to about 90° C., about 90° C. to about 95° C., about 95° C. to about 100° C., about 100° C. to about 105° C., about 105° C. to about 110° C., about 110° C. to about 120° C., or 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C., 116° C., 117° C., 118° C., 119° C., 120° C., 121° C., 122° C., 123° C., 124° C., 125° C., or more.

In some aspects, the polypeptide retains an amylase, or cellulase activity after exposure to a temperature in the range from about −100° C. to about −80° C., about −80° C. to about −40° C., about −80° C. to about −60° C., about −60° C. to about −40° C., about −40° C. to about −20° C., about −20° C. to about 0° C., about 0° C. to about 5° C., about 5° C. to about 15° C., about 15° C. to about 25° C., about 25° C. to about 37° C., about 37° C. to about 45° C., about 45° C. to about 55° C., about 55° C. to about 70° C., about 70° C. to about 75° C., about 75° C. to about 85° C., about 85° C. to about 90° C., about 90° C. to about 95° C., about 95° C. to about 100° C., about 100° C. to about 105° C., about 105° C. to about 110° C., about 110° C. to about 120° C., or 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C., 116° C., 117° C., 118° C., 119° C., 120° C., 121° C., 122° C., 123° C., 124° C., 125° C., or more, at about pH 3.0, about pH 3.5, about pH 4.0, about pH 4.5, about pH 5.0, about pH 5.5, about pH 6.0, about pH 6.5, about pH 7.0, about pH 7.5, about pH 8.0, about pH 8.5, about pH 9.0, about pH 9.5, about pH 10.0, about pH 10.5, about pH 11.0, about pH 11.5, about pH 12.0 or more.

The invention can be practiced using nucleic acids encoding polypeptides having amylase or a cellulase activity, wherein the nucleic acids comprise a sequence that hybridizes under stringent conditions to a sequence as set forth in SEQ ID NO:1, SEQ ID NO:5, SEQ ID NO:7, SEQ ID NO:9, SEQ ID NO:11, SEQ ID NO:13, and/or SEQ ID NO:15. In some aspects, the nucleic acid encodes a polypeptide having an amylase or a cellulase activity. The nucleic acid can be at least about 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200 or more residues in length or the full length of the gene or transcript. In some aspects, the stringent conditions comprise a wash step comprising a wash in 0.2×SSC at a temperature of about 65° C. for about 15 minutes. The compositions and methods disclosed herein comprise use of isolated, synthetic, or recombinant polypeptides comprising an amino acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:2, SEQ ID NO:6, SEQ ID NO:8, SEQ ID NO:10, SEQ ID NO:12, SEQ ID NO:14 and/or SEQ ID NO:16, or an enzymatically active fragment thereof, wherein such fragments are of at least about 10, 15, 20, 25, 30, 35, 40, 45, 50, 55, 60, 65, 70, 75, 80, 85, 90, 95, 100, 125, 150, 175, 200, 225, 250, 275, 300, 325, 350 or more residues, or over the full length of the polypeptide. In some aspects, the polypeptide has cellulase or amylase activity.

Exemplary polypeptide or peptide sequences used to practice this invention include SEQ ID NO:2, SEQ ID NO:6, SEQ ID NO:8, SEQ ID NO:10, SEQ ID NO:12, SEQ ID NO:14, and/or SEQ ID NO:16, including subsequences (enzymatically active fragments) thereof and variants thereof, e.g., including fragments of at least about 10, 15, 20, 25, 30, 35, 40, 45, 50, 75, 80, 85, 90, 95, 100, 150, 200, 250, 300, 350, 400, 450, 500, 550, 600 or more residues in length, or over the full length of an enzyme.

Assays for measuring amylase activity, or cellulase activity, e.g., for determining if a polypeptide has the desired activity, are well known in the art and are within the scope disclosed herein; see, e.g., Baker W L, Panow A, Estimation of cellulase activity using a glucose-oxidase-Cu(II) reducing assay for glucose, J Biochem Biophys Methods. 1991 December, 23(4):265-73; Sharrock K R, Cellulase assay methods: a review, J Biochem Biophys Methods. 1988 October, 17(2):81-105; Carder J H, Detection and quantitation of cellulase by Congo red staining of substrates in a cupplate diffusion assay, Anal Biochem. 1986 Feb. 15, 153(1)-75-9; Canevascini G., A cellulase assay coupled to cellobiose dehydrogenase, Anal Biochem. 1985 Jun. 30 147(2):419-27; Huang J S, Tang J, Sensitive assay for cellulase and dextranase. Anal Biochem. 1976 Jun. 73(2): 369-77.

In some embodiments, a polypeptide used to practice this invention, whether alone or with a "cocktail" disclosed herein, includes amylases that can catalyze the hydrolysis of polysaccharides comprising glucose monomers, such as starch (a polymer of glucose monomers joined by 1,4-alpha or 1,6-alpha linkages). In some aspects, the polypeptide has an amylase activity, e.g., an alpha amylase activity, endo-amylase activity, or a glucoamylase activity; and the term "amylase" as used herein also includes enzyme activity which catalyzes the hydrolysis of a polysaccharide, e.g., a starch. Amylases used to practice the invention include polypeptides having an α-amylase activity, a α-amylase activity, a glucoamylase activity, a 1,4-α-D-glucan glucohydrolase activity, an exoamylase activity, a glucan α-maltotetrahydrolase activity, a maltase activity, an isomaltase activity, a glucan 1,4, α-glucosidase activity, an α-glucosidase activity, a sucrase activity or an agarase activity (e.g., a α-agarase activity), For example, an amylase used to practice this invention includes polypeptides having α-amylase activity, including the ability to hydrolyze internal alpha-1,4-glucosidic linkages in starch to produce smaller molecular weight malto-dextrins. In some aspects, the alpha-amylase activity includes hydrolyzing internal alpha-1,4-glucosidic linkages in starch at random. An amylase used to practice this invention includes polypeptides having glucoamylase activity, such as the ability to hydrolyse glucose polymers linked by alpha-1,4- and alpha-1,6-glucosidic bonds. In some aspects, an amylase used to practice this invention includes polypeptides having glucoamylase activity, hydrolyzing internal alpha-1,4-glucosidic linkages to yield smaller molecular weight malto-dextrins. An amylase used to practice this invention includes polypeptides having glucan 1,4-alpha-glucosidase activity, or 1,4-alpha-D-glucan glucohydrolase, commonly called glucoamylase but also called amyloglucosidase and alpha-amylase that, in one aspect, releases alpha-D-glucose from 1,4-alpha-, 1,6-alpha- and 1,3-alpha-linked glucans. An amylase used to practice this invention includes polypeptides having exo-amylase activity.

In some embodiments, a polypeptide used to practice this invention, whether alone or with a "cocktail" disclosed herein, includes for example a cellulase or cellulases that can catalyze the hydrolysis of polysaccharides comprising glucose monomers, such as guar gum (a polymer of glucose monomers joined by 1,4-alpha or 1,6-alpha linkages). In some aspects, the polypeptide used to practice this invention, whether alone or with a "cocktail" disclosed herein, includes cellulase enzymes described herein, possess glucanase, e.g., endoglucanase, mannanase, xylanase activity or a combination of these activities. In some aspects, the glucanase activity is an endoglucanase activity (e.g., endo-1,4-beta-D-glucan 4-glucano hydrolase activity) and comprises hydrolysis of 1,4-beta-D-glycosidic linkages in cellulose, cellulose derivatives (e.g., carboxy methyl cellulose and hydroxy ethyl cellulose) lichenin, beta-1,4 bonds in mixed beta-1,3 glucans, such as cereal beta-D-glucans or xyloglucans and other plant material containing cellulosic parts. In alternative aspects, these glucanases e.g., endoglucanases, mannanases, xylanases have increased activity and stability, including thermotolerance or thermostability, at increased or decreased pHs and temperatures.

Examples of suitable polysaccharide substrates include galactomannan gums, guars, derivatized guars, cellulose and cellulose derivatives, starch, starch derivatizes, xanthan, derivatized xanthan, and mixtures thereof. Specific examples also include, but are not limited to, guar gum, guar gum derivative, locust bean gum, karaya gum, xanthan gum, cellulose, and cellulose derivatives, etc. Typical polymeric viscosifiers or gelling agents to which the disclosed enzymes may be directed include guar gum, hydroxypropyl guar, carboxymethyl hydroxypropyl guar, hydroxyethyl cellulose, carboxymethyl hydroxyethyl cellulose, carboxymethyl cellulose, dialkyl carboxymethyl cellulose, etc. Other examples of polymers include, but are not limited to, phosphomannons, scerolglucons, dextrans and other types of polymers. In some embodiments, a polymer substrate is carboxymethyl hydroxypropyl guar. In some embodiments, a disclosed enzyme may also be effective in hydrolyzing biogums (e.g., succinoglycan biogums made from date syrup or sucrose). In some embodiments, a disclosed enzyme may be used to hydrolyze cellulose-containing or derivatized cellulose-containing polymers—typically, the enzymes attack glucosidic linkages of the cellulose backbone. The disclosed enzymes may be suitable for degrading the polymer into mostly monosaccharide units, in some cases, by specifically hydrolyzing the exo(1,4)-β-D-glucosidic and endo(1,4)-β-D-glucosidic linkages between monosaccharide units and the cellulose backbone in the (1,4)-β-D-glucosidic linkages of any cellobiose fragments.

The enzyme-comprising compositions disclosed herein can comprise one polysaccharide-degrading enzyme as described herein, or can comprise a mixture (a "cocktail") of one two, three, four, or more of any of the polysaccharide-degrading polypeptides described herein, including the genus based on SEQ ID NO:2, SEQ ID NO:6, SEQ ID NO:8, SEQ ID NO:10, SEQ ID NO:12, SEQ ID NO:14 and/or SEQ ID NO:16. A composition used to practice the invention can comprise one, two, three or more polypeptides described herein, including the genus based on SEQ ID NO:2, SEQ ID NO:6, SEQ ID NO:8, SEQ ID NO:10, SEQ ID NO:12, SEQ ID NO:14, and/or SEQ ID NO:16 and any combination of other enzymes, such as tryptophanases or tyrosine decarboxylases, laccases, catalases, laccases, other cellulases, endoglycosidases, endo-beta-1,4-laccases, amyloglucosidases, other glucosidases, glucose isomerases, glycosyltransferases, lipases, phospholipases, lipooxygenases, beta-laccases, endo-beta-1,3(4)-laccases, cutinases, peroxidases, amylases, xanthanases, glucoamylases, pectinases, reductases, oxidases, decarboxylases, phenoloxidases, ligninases, pullulanases, arabinanases, hemicellulases, mannanases, xylolaccases, xylanases, pectin acetyl esterases, rhamnogalacturonan acetyl esterases, proteases, peptidases, proteinases, polygalacturonases, rhamnogalacturonases, galactanases, pectin lyases, transglutaminases, pectin methylesterases, other cellobiohydrolases, and/or transglutaminases.

The compositions and methods disclosed herein comprise use of isolated, synthetic or recombinant polypeptides comprising these polypeptides (e.g., the genus of polypeptides as described above), and a signal sequence. The signal sequence can be derived from another amylase, xanthanase, and/or glycosidase, e.g., cellulase or endoglucanase, cellobiohydrolase, mannanase and/or beta-glucosidase enzyme or a noncellulase, e.g., non-endoglucanase, non-cellobiohydrolase, and/or non-beta-glucosidase enzyme (a heterologous) enzyme.

The compositions and methods disclosed herein comprise use of isolated, synthetic, or recombinant polypeptides not containing a signal sequence, or lacking all or part of a signal sequence, or comprising a heterologous signal sequence, such as a heterologous amylase, or xanthanase, or glycosidase, or cellulase, e.g., endoglucanase, cellobiohydrolase, mannanase, and/or beta-glucosidase enzyme signal sequence or, non-amylase, non-xanthanase, or non-cellulase, e.g., non-endoglucanase, noncellobiohydrolase, and/or non-beta-glucosidase enzyme signal sequence.

The compositions and methods disclosed herein comprise use of isolated, synthetic, or recombinant chimeric proteins comprising a first domain comprising a signal sequence and at least a second domain comprising the genus of polypeptides as described above. The protein can be a fusion protein. The second domain can comprise several enzymes or activities. The enzyme can be a non-enzyme. The compositions and methods disclosed herein comprise use of isolated, synthetic, or recombinant chimeric proteins comprising the genus of polypeptides as described above and a signal peptide (SP), a prepro sequence and/or a catalytic domain (CD), and in an alternative embodiment, at least another domain comprising a heterologous polypeptide or peptide, wherein the heterologous polypeptide or peptide is not naturally associated with the signal peptide (SP), prepro sequence and/or catalytic domain (CD). In some aspects, the heterologous polypeptide or peptide is not an amylase, or xanthanase, or cellulase, e.g., endoglucanase, cellobiohydrolase, mannanase and/or beta-glucosidase enzyme. The heterologous polypeptide or peptide can be amino terminal to, carboxy terminal to, or on both ends of the signal peptide (SP), prepro sequence and/or catalytic domain (CD).

In some aspect, an amylase and/or cellulase used to practice this invention can retain enzyme activity under conditions comprising about pH 6.5, pH 6, pH 5.5, pH 5, pH 4.5, pH 4.0, pH 3.5, pH 3.0 or less (more acidic); or, can retain activity under conditions comprising about pH 7, pH 7.5 pH 8.0, pH 8.5, pH 9, pH 9.5, pH 10, pH 10.5, pH 11.0, pH 11.5, pH 12, pH 12.5 or more (more basic); or, can retain enzyme activity after exposure to conditions comprising about pH 6.5, pH 6, pH 5.5, pH 5, pH, 4.5, pH 4.0, pH 3.5, pH 3.0 or less (more acidic); or, can retain enzyme activity after exposure to conditions comprising about pH 7, pH 7.5 pH 8.0, pH 8.5, pH 9, pH 9.5, pH 10, pH 10.5, pH 11.0, pH 11.5, pH 12, pH 12.5 or more (more basic); or, can retain activity at under alkaline conditions. In certain aspects, the pH of the reaction is conducted in the range of about 3.0 to about 9.0. In other aspects, the pH is about 4.5 or the pH is about 7.5 or the pH is about 9. Reaction conditions conducted under alkaline conditions also can be advantageous, e.g., in some industrial applications of enzymes disclosed herein.

The invention provides protein preparations comprising any member of the several genuses of polypeptides (including peptides) described herein, wherein the protein preparation comprises a liquid, a solid or a gel; and any member of the several genuses of polypeptides (including peptides) used to practice this invention can be a heterodimer comprising a polypeptide as described herein, e.g., where the second member of the heterodimer can be a different amylase, or xanthanase, or cellulase, e.g., endoglucanase, cellobiohydrolase, mannanase and/or beta-glucosidase enzyme, a different enzyme or another protein. In some aspects, the second domain can be a polypeptide and the heterodimer can be a fusion protein. In some aspects, the second domain can be an epitope or a tag. In some aspects, the invention provides homodimers comprising a polypeptide used to practice the invention.

The invention can be practiced using immobilized polypeptides (including peptides) having amylase and/or cellulase enzyme activity as described herein; and a polypeptide can have at least one additional (a second) domain. In some aspects, the polypeptide can be immobilized on a cell, a metal, a resin, a polymer, a ceramic, a glass, a microelectrode, a graphitic particle, a bead, a gel, a plate, an array or a capillary tube.

The amylase and/or cellulase used to practice this invention can be prepared by expression of a polynucleotide encoding the enzyme in any organism, e.g., a bacterium, a yeast, a plant, an insect, a fungus and/or an animal. The organism can be, for example, a *P. flourescencs, S. pombe, S. cerevisiae, Pichia pastoris, E. coli, Streptomyces* sp., *Bacillus* sp. or a *Lactobacillus* sp.

The amylase and/or cellulase enzyme, used to practice this invention can be formulated in any enzyme delivery matrix, e.g., comprising a thermostable recombinant enzyme; e.g., as an enzyme delivery matrix in the form of pellets comprising a granulate carrier and a thermostable recombinant enzyme, wherein the pellets readily disperse the enzyme contained therein into aqueous media, and administering the enzyme delivery matrix into the desired environment, e.g., a flowback liquid.

The invention provides compositions and enzymes used in a variety of forms and formulations. In the methods disclosed herein, these enzymes are used in a variety of forms and formulations. For example, purified polypeptides can be used in enzyme preparations deployed in drilling or fracturing applications.

In another embodiment the invention comprises SEQ ID NO:1, wherein said sequence encodes a protein. In a further embodiment the invention comprises a nucleotide sequence encoding a cellulase derived from *Thermotoga maritima*, or SEQ ID NO:3, comprising at least one mutation selected from T6C, T9C, T15G, A22C, G24T, A33C, A39C, A40C, A42C, A54C, A57C, T66C, G81A, A84C, A6C, G6C, A9C, G9C, A15G, C15G, T22C, G22C, A24T, C24T, T33C, G33C, T39C, G039C, T40C, G40C, T42C, G42C, T54C, G54C, T57C, G57C, A66C, G66C, C81A, T81A, T84C, G84C, or any combination thereof, wherein optionally, any such mutations are silent. In a further embodiment of the invention, a least one such silent mutation results in expression of said cellulase at a higher level than a nucleotide sequence lacking at least one such mutation.

In another embodiment of the present invention, the invention comprises a nucleotide sequence from *Thermotoga maritima* having at least one mutation and having an increased expression level of a protein encoded by said nucleotide sequence compared to a *Thermotoga maritima* wild-type genomic sequence, wherein optionally, said mutations is silent.

In another embodiment of the present invention, the invention comprises a first nucleotide sequence encoding the polypeptide of SEQ ID NO:2 wherein said nucleotide sequence has been mutated with respect to a second sequence encoding SEQ ID NO:2 such that the expression level of said protein is increased relative to that of said protein encoded by said second nucleotide sequence.

In another embodiment of the present invention, the invention comprises a nucleotide sequence encoding a protein at least 50%, 60%, 70%, 80%, 90%, 95%, 97%, 98%, 99% or 100% identical to SEQ ID NO:2, or a fragment thereof, wherein said nucleotide sequence comprises at least one mutation selected from T6C, T9C, T15G, A22C, G24T, A33C, A39C, A40C, A42C, A54C, A57C, T66C, G81A, A84C, A6C, G6C, A9C, G9C, A15G, C15G, T22C, G22C, A24T, C24T, T33C, G33C, T39C, G39C, T40C, G040C, T42C, G42C, T54C, G54C, T57C, G57C, A66C, G66C, C81A, T81A, T84C, G84C, or any combination thereof.

In another embodiment of the present invention, any of the proteins of the invention are expressed in bacterial expression systems, wherein the bacteria expression system is a gram-negative bacteria expression system, e.g., *Pseudomonas, E. coli, Ralstonia*, or *Caulobacter* expression system.

In another embodiment of the present invention, expression of the cellulase of the invention is produced at least 1.0 g/L, 2.0 g/L, 3.0 g/L, 4.0 g/L, 5.0 g/L, 6.0 g/L, 7.0 g/L, 8.0 g/L, 9.0 g/L, 10.0 g/L, 11.0 g/L, 12.0 g/L, 13.0 g/L, 14.0 g/L, 15.0 g/L, 16.0 g/L, 17.0 g/L, 18.0 g/L, 19.0 g/L, 20.0 g/L, 21.0 g/L, 22.0 g/L, 23.0 g/L, 24.0 g/L, 25.0, g/L, 26.0 g/L, 27.0 g/L, 28.0 g/L, 29.0 g/L, 30.0 g/L, 31.0 g/L, 32.0 g/L, 33.0 g/L, 34.0 g/L, or 35.0 g/L.

In another embodiment of the present invention, a cellulase of the present invention is combined with a second enzyme wherein the second enzyme is selected from the group consisting of a lactase, a lipase, a protease, a catalase, a xylanase, a cellulase, a glucanase, a mannanase, an amylase, an amidase, an epoxide hydrolase, an esterase, phospholipase, transaminase, an amine oxidase, cellobiohydrolase, an ammonia lyase, or any combination thereof.

In another embodiment of the present invention, the invention comprises an isolated, recombinant, or synthetic nucleotide, having a nucleic acid sequence comprising SEQ ID NO:1, wherein the nucleic acid sequence encodes a polypeptide having a cellulase activity.

In another embodiment of the present invention, the invention comprises an isolated, recombinant, or synthetic nucleotide, comprising a nucleic acid sequence of SEQ ID NO:1, wherein the nucleic acid sequence encodes a polypeptide having a cellulase activity and the polypeptide comprises an amino acid sequence of SEQ ID NO:2, or an enzymatically active fragment thereof.

In another embodiment of the present invention, the invention comprises, an isolated, recombinant, or synthetic nucleic acid sequence comprising SEQ ID NO:1 that encodes a polypeptide having a cellulase activity, wherein the polypeptide comprises an amino acid sequence of SEQ ID NO:2 and the polypeptide is produced in a recombinant *Pseudomonas fluorescens* expression system.

In another embodiment of the present invention, the invention comprises a method for treating flowback fluids, used in or produced by oil or gas operations comprising: (a) providing an enzyme or enzyme treatment to a flowback fluid; (b) allowing the enzyme or enzyme treatment to degrade a polysaccharide- or starch-comprising material in the flowback fluid, wherein the enzyme or enzyme treatment is effective to break down or hydrolyze the polysaccharide- or starch-comprising material in the flowback fluid, wherein optionally the enzyme is a cellulase or an amylase. In further embodiment of the method for treating flowback fluids, the enzyme or enzyme treatment comprises and amylase wherein the amylase comprises a polypeptide having an amino acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:16, or an enzymatically active fragment thereof. In further embodiment of the method for treating flowback fluids, the enzyme or enzyme treatment comprises and cellulase wherein the cellulase comprises a polypeptide having an amino acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to SEQ ID NO:4, SEQ ID NO:6, SEQ ID NO:8, SEQ ID NO:10, SEQ ID NO:12 and/or SEQ ID NO:14, or an enzymatically active fragment thereof.

In another embodiment of the present invention, the invention comprises, a composition comprising a polymeric viscosifier, a surfactant, a thermostabilizer, and an enzyme breaker comprising a wild-type cellulase derived from a hyperthermophilic bacterium or a mutated variant thereof. In further embodiment of the composition, the viscosifier is a guar gel comprising a linear guar, a crosslinked guar, or mixtures thereof. In further embodiment of the composition the enzyme breaker specifically hydrolyzes β-1,4 glycosidic bonds in the guar gel. In further embodiment of the composition the enzyme breaker does not specifically hydrolyze α-1,6 glycosidic bonds in the guar gel. In further embodiment of the composition the enzyme breaker retains its ability to hydrolyze β-1,4 glycosidic bonds in the guar gel at temperatures up to about 275° F. In further embodiment of the composition wherein the enzyme breaker retains its ability to hydrolyze β-1,4 glycosidic bonds in the guar gel at a pH of up to about 11. In further embodiment of the composition, the enzyme breaker has SEQ ID. NO. 2. In further embodiment of the composition, the enzyme breaker is encoded by a polynucleotide having SEQ ID. NO. 1. In further embodiment of any of the above compositions, the enzyme breaker is a mutated variant of the wild-type cellulase, and has a melting temperature that is at least 20° F. greater than the melting temperature of the wild type cellulase at about pH 6.5 and at least 10° F. greater than the melting temperature of the wild type cellulase at about pH 10.5. In further embodiment of any of the above compositions, further comprising an ester wherein optionally the ester is selected from the group comprising ethylacetate, 2-ethoxyethyl acetate, ethyl acetoacetate, methylbenzoate, ethylformate, methylacetate, and dimethylphthalatea.

In another embodiment, the present invention comprises an animal feed or animal feed additive comprising the polypeptide encoded by SEQ ID NO 1. In another embodiment the animal feed or animal feed additive assists or aids in the digestion of foodstuffs.

All publications, patents, patent applications, GenBank sequences and ATCC deposits, cited herein are hereby expressly incorporated by reference for all purposes in their respective entireties.

DETAILED DESCRIPTION

*Thermotoga maritima* is a thermophilic eubacteria characterized by its ability to grow in extreme salt concentrations (i.e., from 0.25% NaCl to 6.00% NaCl). *Thermotoga maritima* belongs to the order Thermotogales whose members are thermophilic, rod-shaped, anaerobic and gram-negative. The minimum temperature for growth is around 55° C., optimum is 80°-85° C., and maximum is about 90° C. In some embodiments, the minimum temperature is less than 55° C. and the maximum temperature is greater than 90° C. These bacteria have slowly evolved from one of the deepest branches in the kingdom of eubacteria. Members of Thermotogales have been described as "wide-spread and cosmopolitan" (Huber, R. et al., 2006), thriving in active geothermal areas. *Thermotoga maritima* is closely related to the species *Thermotoga neapolitana, Thermotoga petrophila*, and *Thermotoga naphthophila*. Specimens of *Thermotoga maritima* have been obtained from sea floors in Vulcano, Italy; Riberia Quente and Sao Miguel Island, Azores; Sangeang Island, Indonesia; and Fiji Island. (Huber, R. et al., 2006).

Strain MSB8 was isolated from a geothermally heated marine sediment at Vulcano, Italy (Huber, 1986). The temperature at the collection site ranged from 70-100° C., with a pH of 6.5-7.0. The strain has been deposited at the Deutsche Sammlung von Mikroorganismen as DSM 3109 and at ATCC as ATCC43589 (Huber, R. et at, 2006).

*Thermotoga maritima* strain MSB8 has been studied for its enzyme encoding genes due to the exceptional thermostability of the enzymes it produces. Liebl (Liebl, W. et al., 1996) has published an "Analysis of a *Thermotoga maritima* DNA fragment encoding two similar thermostable cellulases, CelA and CelB, and characterization of the recombinant enzymes." Additionally, genes for amylolytic enzymes (Bibel, M. et al., 1998), reverse gyrase (Bouthier de la Tour, C. et al., 1998), alpha-amylase (Liebl, W. et al., 1997), alpha-glucuronidase (Ruile, P. et al., 1997), xylanase (Winterhalter, C. et al., 1995), beta-glucosidase (Liebl, W. et al., 1994), glucanotransferase (Liebl, W. et al., 1992) have been isolated and analyzed. A study by Bronnenmeier (Bronnenmeier, K. et al., 1995), "Purification of *Thermotoga maritima* enzymes for the degradation of cellulosic materials" has shown that these enzymes are of value for degrading cellulose and xylan.

Expression Systems

In some embodiments, the DNA encoding the cellulase of the present invention may be introduced, either on a plasmid or stably transformed into the genome of, for example, any number of gram negative bacterial systems such as *E. coli, Pseudomonas* species such as *fluorescens, Pseudomonas putida, Pseudomonas aeruginosa, Ralstonia* species, or *Caulobacter* species. Similarly, the cellulase may be introduced into any number of gram positive bacterial expression systems such as *Bacillus* species such as *Bacillus subtilis, Bacillus megaterium, Bacillus brevis, Lactococcus* species such as *Lactococcus lactis, Lactobacillus* species, *Streptomyces* species such as *Streptomyces lividans*. Other gram negative, gram positive or unrelated eubacterial or archaeal expression systems may be used to express the cellulase.

Polypeptides used to practice this invention can be expressed in a microorganism using procedures known in the art. In other aspects, the polypeptides used to practice this invention can be immobilized on a solid support prior to use in the methods disclosed herein. Methods for immobilizing enzymes on solid supports are commonly known in the art, for example J. Mol. Cat. B: Enzymatic 6 (1999) 29-39; Chivata et al. Biocatalysis: Immobilized cells and enzymes, J Mol. Cat. 37 (1986) 1-24: Sharma et al., Immobilized Biomaterials Techniques and Applications, Angew. Chem. Int. Ed. Engl. 21 (1982) 837-15 54: Laskin (Ed.), Enzymes and Immobilized Cells in Biotechnology. Polypeptides used to practice this invention can be recombinantly expressed. Polypeptides used to practice this invention can include recombinant proteins encoded by a genus of nucleic acids based on SEQ ID NO:1, SEQ ID NO:5, SEQ ID NO:7, SEQ ID NO:9, SEQ ID NO:11, SEQ ID NO:13 and/or SEQ ID NO:15 (to encode, e.g., SEQ ID NO:2, SEQ ID NO:6, SEQ ID NO:8, SEQ ID NO:10, SEQ ID NO:12, SEQ ID NO:14 and/or SEQ ID NO:16).

The exemplary polypeptides SEQ ID NO:2, SEQ ID NO:6, SEQ ID NO:8, SEQ ID NO:10, SEQ ID NO:12, SEQ ID NO:14 and/or SEQ ID NO:16 (encoded, e.g., by SEQ ID NO:1, SEQ ID NO:5, SEQ ID NO:7, SEQ ID NO:9, SEQ ID NO:11, SEQ ID NO:13 and/or SEQ ID NO:15 respectively) can be useful for breaking (or hydrolysis) of beta-linked carbohydrates such as guar gum, derivatized guar (hydroxypropyl guar, carboxymethyl guar, carboxymethyl hydroxypropyl guar), and carboxymethyl cellulose. The action pattern of the enzymes includes both endoglycosidase and exoglycosidase activities, allowing them to effectively reduce viscosity by cleaving within long polysaccharide chains and also by cleaving disaccharide units from the ends of the polymers. They also have broad spectrum mannanase activity.

In some embodiments, SEQ ID NO:1 is used to direct an increased level of expression in a number of systems in which the disclosed cellulase protein may be expressed. SEQ ID NO:1 may be introduced into any number of expression systems to express the disclosed cellulase at an improved accumulation level. For example, SEQ ID NO:1 may be introduced, either on a plasmid or stably transformed into the genome of, for example, any number of gram negative bacterial systems such as *E. coli, Pseudomonas* species such as *fluorescens, Pseudomonas putida, Pseudomonas aeruginosa, Ralstonia* species, or *Caulobacter* species. Similarly, SEQ ID NO:1 may be introduced into any number of gram positive bacterial expression systems such as *Bacillus* species such as *Bacillus subtilis, Bacillus megaterium, Bacillus brevis, Lactococcus* species such as *Lactococcus lactis, Lactobacillus* species, *Streptomyces* species such as *Streptomyces lividans*. Other gram negative, gram positive or unrelated eubacterial or archaeal expression systems may be used to express SEQ ID NO:1. In a further embodiment, SEQ ID NO:1 may be introduced into any number of eukaryotic expression systems such as *Saccharomyces, Schizosaccharomyces pombe, Pichia pastoris*, and *Hansanuela polymorpha*.

More specifically, SEQ ID NO:1 may be introduced into a plasmid to direct its expression. Plasmids which SEQ ID NO:1 may be introduced include, for example, *E. coli* expression vectors of the families pQE, pET, and pASK; *Pseudomonas* expression vectors of the families pCN51 LT8, RSF1010, pWZ112T, and pMYC; *Bacillus* expression vectors of the families pBAX, pHT01, and pHIS1525; *Streptomyces* expression vectors of the families pIJ6021 and pIJ2460; and *Lactococcus*: expression vectors of the families pNZ9530 and pNZ8148, for example. These examples are for demonstrative purposes and do not represent a complete set of vectors in which the polynucleotide sequence of SEQ ID NO:1 can be expressed.

In some embodiments, the expression system could be any *Pseudomonas fluorescens* expression system known in the art, for example, the *Pseudomonas fluorescens* expression system that is commercially available from Dow Global Technologies Inc., strain DC454 (US Patent PUB. APP. NO. 20050130160 and US Patent PUB. APP. NO. 20050186666). A nucleic acid sequence encoding the cellulase enzyme or polypeptide is inserted either in the pMYC vector (Dow Global Technologies Inc., U.S. Pat. PUB. APP. NO. 20050130160) or in the pDOW1169 vector (Dow Global Technologies Inc., U.S. Pat. PUB. APP. NO. 20080058262) and then introduced into the *Pseudomonas fluorescens* host by electroporation. Those skilled in the art will know alternative vectors that can be used as embodiments of this invention.

In some embodiments, the cellulase will be expressed at least at the following expression levels: 1.0 g/L 2.0 g/L, 3.0 g/L, 4.0 g/L, 0.5.0 g/L, 6.0 g/L, 7.0 g/L, 8.0 g/L, 9.0 g/L, 10.0 g/L, 11.0 g/L, 12.0 g/L, 13.0 g/L, 14.0 g/L, 15.0 g/L, 16.0 g/L, 17.0 g/L, 18.0 g/L, 19.0 g/L, 20.0 g/L, 21.0 g/L, 22.0 g/L, 23.0 g/L, 24.0 g/L, 25.0, g/L, 26.0 g/L, 27.0 g/L, 28.0 g/L, 29.0 g/L, 30.0 g/L, 31.0 g/L, 32.0 g/L, 33.0 g/L, 34.0 g/L, 35.0 g/L, or more.

Nucleic Acid

The invention provides isolated, synthetic, or recombinant nucleic acids comprising sequences completely complementary to the nucleic acid sequences disclosed herein (complementary (non-coding) and coding sequences also hereinafter collectively referred to as nucleic acid sequences disclosed herein).

The invention provides isolated, synthetic, or recombinant nucleic acids comprising a nucleic acid encoding at least one polypeptide having a cellulolytic activity, wherein the nucleic acid comprises a sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or complete (100%) sequence identity (homology) to an exemplary nucleic acid disclosed herein, including the sequence of SEQ ID NO:1, SEQ ID NO:5, SEQ ID NO:7, SEQ ID NO:9, SEQ ID NO:11, SEQ ID NO:13, and/or SEQ ID NO:15. For example, the invention provides isolated, synthetic or recombinant nucleic acids comprising a nucleic acid sequence SEQ ID NO:1 (an exemplary polynucleotide sequence of this invention). The invention provides isolated, synthetic, or recombinant nucleic acids encoding a polypeptide comprising a sequences as set forth in SEQ ID NO:2, SEQ ID NO:6, SEQ ID NO:8, SEQ ID NO:10, SEQ ID NO:12, SEQ ID NO:14 and/or SEQ ID NO:16 (exemplary polypeptide sequences of this invention), and enzymatically active fragments thereof.

Polypeptide

Polypeptides and peptides disclosed herein are isolated, synthetic, or recombinant polypeptides. Peptides and proteins can be recombinantly expressed in vitro or in vivo. The peptides and polypeptides disclosed herein can be made and isolated using any method known in the art. Polypeptides and peptides disclosed herein can also be synthesized, whole or in part, using chemical methods well known in the art. For example, cellulase polypeptides can be produced in a standard recombinant expression system (as described herein), chemically synthesized, or purified from organisms in which they are naturally expressed.

The invention provides isolated, synthetic, or recombinant polypeptides having cellulolytic activity comprising an amino acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or has 100% (complete) sequence identity to an exemplary amino acid sequence disclosed herein (e.g., SEQ ID NO:2, SEQ ID NO:6, SEQ ID NO:8, SEQ ID NO:10, SEQ ID NO:12, SEQ ID NO:14 and/or SEQ ID NO:16), or an enzymatically active fragment thereof.

The invention provides isolated, synthetic, or recombinant polypeptides comprising a sequence as set forth in SEQ ID NO: 2, SEQ ID NO:6, SEQ ID NO:8, SEQ ID NO:10, SEQ ID NO:12, SEQ ID NO:14 and/or SEQ ID NO:16, and enzymatically active fragments thereof, and variants thereof.

In alternative embodiments, the invention provides polypeptides (and the nucleic acids that encode them) having cellulolytic activity but lacking a signal sequence, a prepro domain, a dockerin domain, and/or a carbohydrate binding module (CBM); and in one aspect, the carbohydrate binding module (CBM) comprises, or consists of, a cellulose binding module, a lignin binding module, a xylan binding module, a xylose binding module, a mannose binding module, a xyloglucan-specific module, and/or a arabinofuranoside binding module.

In alternative embodiments, the invention provides polypeptides (and the nucleic acids that encode them) having a cellulolytic activity further comprising a heterologous sequence; and in one aspect, the heterologous sequence comprises, or consists of a sequence encoding: (i) a heterologous signal sequence, a heterologous carbohydrate binding module, a heterologous dockerin domain, a heterologous catalytic domain (CD), or a combination thereof; (ii) the sequence of (i), wherein the heterologous signal sequence, carbohydrate binding module or catalytic domain (CD) is derived from a heterologous enzyme; or, (iii) a tag, an epitope, a targeting peptide, a cleavable sequence, a detectable moiety or an enzyme; and in one aspect, the heterologous carbohydrate binding module (CBM) comprises, or consists of, cellulose binding module, a lignin binding module, a xylan binding module, a xylose binding module, a mannose binding module, a xyloglucan-specific module and/or a arabinofuranoside binding module; and in one aspect, the heterologous signal sequence targets the encoded protein to a vacuole, the endoplasmic reticulum, a chloroplast or a starch granule.

Enzymatic Activity

The enzymatic hydrolysis of pNP-β-D-lactopyranoside by the disclosed cellulase can be used as a measure of activity of an enzyme disclosed herein such as SEQ ID NO:2, SEQ ID NO:6, SEQ ID NO:8, SEQ ID NO:10, SEQ ID NO:12, The liberation of p-nitrophenol can be followed spectrophotometrically at 405 nm. The increase in absorbance at 405 nm can be converted to μmoles of p-nitrophenol by using a standard absorbance at those defined conditions. One unit of activity is defined as the quantity of enzyme required to liberate 0.42 μmole of p-nitrophenol from 2 mM pNP-β-D-lactopyranoside during one minute at pH 7.00 and 80° C. (Advances in Carbohydrate Chemistry and Biochemistry, Academic Press, 1999)

Thermostability

In some aspects, the recombinant nucleic acid of the present invention encodes a polypeptide having a cellulolytic activity that is thermostable. For example, a polypeptide disclosed herein, SEQ ID NO:2, SEQ ID NO:6, SEQ ID NO:8, SEQ ID NO:10, SEQ ID NO:12, SEQ ID NO:14 and/or SEQ ID NO:16 or the variant evolved enzymes disclosed herein can be thermostable. The thermostable polypeptide according to the invention can retain binding and/or enzymatic activity, e.g., cellulolytic activity, a under conditions comprising a temperature in the range from greater than 37° C. to about 95° C. or between about 55° C. to about 85° C., or between about 70° C. to about 75° C., or between about 70° C. to about 95° C., between about 90° C. to about 95° C., between about 95° C. to about 105° C., or between about 95° C. to about 110° C. In some aspects, wherein the polypeptide can retain binding and/or enzymatic activity, e.g., cellulolytic activity, under conditions comprising 1° C. to about 5° C., between about 5° C. to about 15° C., between about 15° C. to about 25° C., between about 25° C. to about 37° C. In some aspects polypeptides disclosed herein can retain binding and/or enzymatic activity, e.g., cellulolytic activity, under conditions comprising 90° C., 91° C., 92° C., 93° C., 94° C., 95° C., 96° C., 97° C., 98° C., 99° C., 100° C., 101° C., 102° C., 103° C., 103.5° C., 104° C., 105° C., 107° C., 108° C., 109° C. or 110° C., or more. In some embodiments, the thermostable polypeptides according to the invention retains activity, e.g., a cellulolytic activity at a temperature in the ranges described above, under acidic conditions comprising about pH 6.5, pH 6, pH 5.5, pH 5, pH 4.5 or pH 4 or less (more acidic), or, retain a cellulolytic activity after exposure to acidic conditions comprising about pH 6.5, pH 6, pH 5.5, pH 5, pH 4.5 or pH 4 or less (more acidic); or, retain activity under basic conditions comprising about pH 7, pH 7.5 pH 8.0, pH 8.5, pH 9, pH 9.5, pH 10, pH 10.5, pH 11, pH 11.5, pH 12, pH 12.5 or more (more basic) or, retain a cellulolytic activity after exposure to basic conditions comprising about pH 7, pH 7.5 pH 8.0, pH 8.5, pH 9, pH 9.5, pH 10, pH 10.5, pH 11, pH 11.5, pH 12, pH 12.5 or more (more basic).

Thermotolerance

In some aspects, the recombinant nucleic acid of the present invention encodes a polypeptide having a cellulolytic activity that is thermotolerant. For example, a polypeptide disclosed herein, SEQ ID NO:2, SEQ ID NO:6, SEQ ID NO:8, SEQ ID NO:10, SEQ ID NO:12, SEQ ID NO:14 and/or SEQ ID NO:16, or the variant evolved enzymes disclosed herein can be thermotolerant. In some aspects, the cellulolytic activity is thermotolerant, e.g., wherein the polypeptide retains cellulolytic activity after exposure to a temperature in the range from greater than 37° C. to about 95° C., or between about 55° C. to about 85° C., or between about 70° C. to about 75° C., or between about 70° C. to about 95° C., between about 90° C. to about 95° C., between about 95° C. to about 105° C., or between about 95° C. to about 110° C. In some aspects, wherein the polypeptide retain a cellulolytic activity after exposure to conditions comprising a temperature range of between about 1° C. to about 5° C., between about 5° C. to about 15° C., between about 15° C. to about 25° C., between about 25° C. to about 37° C. In some aspects polypeptides disclosed herein can retain a cellulolytic activity after exposure to a temperature up to 90° C., 91° C., 92° C., 93° C., 94° C., 95° C., 96° C., 97° C., 98° C., 99° C., 100° C., 101° C., 102° C., 103° C., 104° C., 105° C., 107° C., 108° C., 109° C. or 110° C., or more. In some aspects, the polypeptides encoded by nucleic acids disclosed herein retain cellulolytic activity under acidic conditions comprising about pH 6.5, pH 6, pH 5.5, pH 5, pH 4.5 or pH 4 or less (more acidic), or, retain a cellulolytic activity after exposure to acidic conditions comprising about pH 6.5, pH 6, pH 5.5, pH 5, pH 4.5 or pH 4 or less (more acidic); or, retain activity under basic conditions comprising about pH 7, pH 7.5 pH 8.0, pH 8.5, pH 9, pH 9.5, pH 10, pH 10.5, pH 11, pH 11.5, pH 12, pH 12.5 or more (more basic).

Cellulosic Digestion

In some aspects, the compositions and methods disclosed herein are used in the enzymatic digestion of biomass and can comprise use of many different enzymes, including the cellulases and hemicellulases. Cellulases used to practice the invention can digest cellulose to glucose. In some aspects, compositions used to practice the invention can include mixtures of enzymes, e.g., xylanases, xylosidases (e.g., β-xylosidases), cellobiohydrolases, and/or arabinofuranosidases, or other enzymes that can digest hemicelluloses, cellulose, and lignocellulosic material, to fermentable sugars and/or to monomer sugars.

Enzymes, e.g., endoglucanases, disclosed herein are used to digest cellulose or any beta-1,4-linked glucan-comprising synthetic or natural material, including those found in any plant material. Enzymes, e.g., endoglucanases, disclosed herein are used as commercial enzymes to digest cellulose from any source, including all biological sources, such as plant biomasses, e.g., corn, grains, grasses (e.g., Indian grass, such as *Sorghastrum nutans*; or, switch grass, e.g., *Panicum* species, such as *Panicum virgatum*), or, woods or wood processing byproducts, e.g., in the wood processing, pulp and/or paper industry, in textile manufacture and in household and industrial cleaning agents, and/or in biomass waste processing.

Dietary

In some embodiments, the cellulase of the present invention may be used to pre-treat, modify, or digest a food, food additive, or dietary supplement for animals or human beings. In some embodiments, the cellulase of the present invention may be used as a food, food additive, or dietary supplement for animals or human beings. In some aspects the cellulase will treat or will act as a prophylaxis for digestive disorders. In some aspects of the present invention the cellulase will alter or enhance digestion. In some aspects of the present invention the cellulase will enhance, alter, or aid in the digestion of foodstuffs. In a further aspect disclosed herein the cellulase will enhance, aid, or alter the nutrient value of foodstuffs. In a further aspect, the cellulase is active in the digestive tract, e.g., in a stomach and/or intestine, for example.

In some embodiments, the cellulase disclosed herein may be used as an animal feed or an animal feed additive. In some embodiments the thermostability and or thermotolerance of the cellulase allows for the formation of pellets without the need for a secondary agent such as salt or wax. An animal feed comprising a cellulase can be provided to an animal in any formulation known to those skilled in the art. Examples of animal feed formulations include, but are not limited to a delivery matrix, a pellet, a tablet, a gel, a liquid, a spray, ground grain, or a powder.

The invention provides edible enzyme delivery matrix comprising a thermostable recombinant cellulase enzyme, e.g., a polypeptide disclosed herein. The invention provides methods for delivering a cellulase supplement to an animal, the method comprising: preparing an edible enzyme delivery matrix in the form of pellets comprising a granulate edible carrier and a thermostable recombinant cellulase enzyme, wherein the pellets readily disperse the cellulase enzyme contained therein into aqueous media, and administering the edible enzyme delivery matrix to the animal. The recombinant cellulase enzyme can comprise a polypeptide disclosed herein. The granulate edible carrier can comprise a carrier selected from the group consisting of a grain germ, a grain germ that is spent of oil, a hay, an alfalfa, a timothy, a soy hull, a sunflower seed meal and a wheat midd. The edible carrier can comprise grain germ that is spent of oil. The cellulase enzyme can be glycosylated to provide thermostability at pelletizing conditions. The delivery matrix can be formed by pelletizing a mixture comprising a grain germ and a cellulase. The pelletizing conditions can include application of steam. In some embodiments, the pelletizing conditions can comprise application of a temperature in excess of about 80° C. for about 5 minutes and the enzyme retains a specific activity of at least 350 to about 900 units per milligram of enzyme.

Methods of Making Ethanol

The invention provides methods for making ethanol comprising contacting a starch-comprising composition with a polypeptide having a cellulolytic activity, such as the enzyme of SEQ ID NO:2, SEQ ID NO:6, SEQ ID NO:8, SEQ ID NO:10, SEQ ID NO:12, and/or SEQ ID NO:14 wherein the polypeptide has a sequence disclosed herein, or the polypeptide is encoded by a nucleic acid comprising a sequence disclosed herein, or an enzymatically active fragment thereof. The invention provides compositions comprising a starch and a polypeptide having a cellulolytic activity, wherein the polypeptide has a sequence disclosed herein, or the polypeptide is encoded by a nucleic acid comprising a sequence disclosed herein, or an enzymatically active fragment thereof.

Brewing and Fermenting

The invention provides methods of brewing (e.g., fermenting) beer comprising the cellulase disclosed herein. In one exemplary process, starch-containing raw materials are disintegrated and processed to form a malt. An enzyme disclosed herein is used at any point in the fermentation process. The cellulase disclosed herein can be used in the brewing industry for the degradation of beta-glucans. In some aspects, the cellulases disclosed herein are used in the brewing industry for the clarification of the beverage. Enzymes disclosed herein can be used in the beverage industry in improving filterability of wort or beer, as described, e.g., in U.S. Pat. No. 4,746,517.

In some aspects, the cellulase disclosed herein is used in mashing and conversion processes. In the brewing and fermentation industries, mashing and conversion processes are performed at temperatures that are too low to promote adequate degradation of water-soluble glucans, mannans, arabinoxylans or xylans, or other polysaccharides. These polymers form gummy substrates that can cause increased viscosity in the mashing wort, resulting in longer mash run-off, residual haze and precipitates in the final beer product due to inefficient filtration and low extraction yield.

In some aspects, the cellulase disclosed herein are used in malthouse operations, e.g., glucanase is added to the process water, to shorten germination times and/or to encourage conversion of poor quality barley to acceptable malts. In some aspects, enzymes disclosed herein are used for mashing, e.g., they are added to increase wort filterability and/or improve lautering (separating the wort from the mash). In some aspects, enzymes disclosed herein are used in the fermentor and/or settling tank to, e.g., assist in haze clearing and/or to improve filtration. In some aspects, enzymes disclosed herein are used in adjunct brewing, e.g., a glucanase disclosed herein is added to breakdown glucans, mannans, arabinoxylans or xylans, or other polysaccharides from barley, wheat, and/or other cereals, including glycans in malt. In some aspects, enzymes disclosed herein are used in malt brewing, e.g., a glucanase disclosed herein is added to modify poor malts with high glucan content.

The cellulase disclosed herein can be used in any beer or alcoholic beverage producing process, as described, e.g., in U.S. Pat. Nos. 5,762,991; 5,536,650; 5,405,624; 5,021,246; 4,788,066, each of which is hereby incorporated by reference in its entirety.

Treating Foods and Food Processing

The cellulases disclosed herein have numerous applications in food processing industry. For example, in one aspect, the enzymes disclosed herein are used to improve the extraction of oil from oil-rich plant material, e.g., oil-rich seeds, for example, soybean oil from soybeans, olive oil from olives, rapeseed oil from rapeseed and/or sunflower oil from sunflower seeds.

The cellulase disclosed herein can be used for separation of components of plant cell materials. For example, enzymes disclosed herein can be used in the separation of glucan-rich material (e.g., plant cells) into components. In some aspects, enzymes disclosed herein can be used to separate glucan-rich or oil-rich crops into valuable protein and oil and hull fractions. The separation process may be performed by use of methods known in the art.

The cellulase disclosed herein can be used in the preparation of fruit or vegetable juices, syrups, extracts and the like to increase yield. The enzymes disclosed herein can be used in the enzymatic treatment (e.g., hydrolysis of glucan-comprising plant materials) of various plant cell wall-derived materials or waste materials, e.g. from cereals, grains, wine or juice production, or agricultural residues such as vegetable hulls, bean hulls, sugar beet pulp, olive pulp, potato pulp, and the like. The enzymes disclosed herein can be used to modify the consistency and appearance of processed fruit or vegetables. The enzymes disclosed herein can be used to treat plant material to facilitate processing of plant material, including foods, facilitate purification or extraction of plant components. The cellulase disclosed herein can be used to improve feed value, decrease the water binding capacity, improve the degradability in waste water plants and/or improve the conversion of plant material to ensilage, and the like. The cellulase disclosed herein can also be used in the fruit and brewing industry for equipment cleaning and maintenance.

Detergent Compositions

The invention provides detergent compositions comprising one or more polypeptides disclosed herein and methods of making and using these compositions. The invention incorporates all methods of making and using detergent compositions, see, e.g., U.S. Pat. Nos. 6,413,928; 6,399,561; 6,365,561; 6,380,147, each of which is hereby incorporated by reference in its entirety. The detergent compositions can be a one and two part aqueous composition, a non-aqueous liquid composition, a cast solid, a granular form, a particulate form, a compressed tablet, a gel and/or a paste and a slurry form. The invention also provides methods capable of a rapid removal of gross food soils, films of food residue and other minor food compositions using these detergent compositions. Enzymes disclosed herein can facilitate the removal of starchy stains by means of catalytic hydrolysis of the starch polysaccharide. Enzymes disclosed herein can be used in dishwashing detergents in textile laundering detergents. The actual active enzyme content depends upon the method of manufacture of a detergent composition and is not critical, assuming the detergent solution has the desired enzymatic activity. In some aspects, the amount of glucosidase present in the final solution ranges from about 0.001 mg to 0.5 mg per gram of the detergent composition. The particular enzyme chosen for use in the process and products of this invention depends upon the conditions of final utility, including the physical product form, use pH, use temperature, and soil types to be degraded or altered. The enzyme can be chosen to provide optimum activity and stability for any given set of utility conditions. The detergents disclosed herein can comprise, for example, cationic, semi-polar nonionic, or zwitterionic surfactants; or, mixtures thereof.

The present invention provides cleaning compositions including detergent compositions for cleaning hard surfaces, detergent compositions for cleaning fabrics, dishwashing compositions, oral cleaning compositions, denture cleaning compositions, and contact lens cleaning solutions. In some aspects, the invention provides a method for washing an object comprising contacting the object with a polypeptide disclosed herein under conditions sufficient for washing. A polypeptide disclosed herein may be included as a detergent additive. The detergent composition disclosed herein may, for example, be formulated as a hand or machine laundry detergent composition comprising a polypeptide disclosed herein. A laundry additive suitable for pre-treatment of stained fabrics can comprise a polypeptide disclosed herein. A fabric softener composition can comprise a polypeptide disclosed herein. Alternatively, a polypeptide disclosed herein can be formulated as a detergent composition for use in general household hard surface cleaning operations.

Oil and Gas Exploration and Clean-Up

To increase the productivity of oil and gas wells and shale gas reservoirs, a highly specialized technique called "hydraulic fracturing" is being increasingly utilized. In a typical hydraulic fracturing operation, large volumes of guar-based fluid (in gel form and referred to as "fracturing fluid") are pumped into the wellbore under very high hydrostatic pressure. The pressurized fluid creates new fissures and fractures in the formation surrounding the wellbore. The sand particles contained in the fracturing fluid move and settle into the newly-created fractures and function to prop these channels open thus increasing oil and gas flow. Once the sand is deposited into the fractures, the gel has to be degraded (i.e., broken down) and brought back up to the surface so as to remove any blockage to the flow of oil or gas. Industry uses viscosity breakers (such as oxidizers, acids, or enzymes) to degrade the fracturing fluid and to remove any solid gel residue from the fissures and fractures.

During typical oil and gas drilling operations liquid is pumped through the drill shaft and exits above the drill bit, such liquid is commonly referred to as "drilling fluid." The drilling fluid serves to cool the bit, add pressure to the bit, lubricate the drill bit, and to remove debris away from drilling site. Drilling debris is carried back to the surface by the fluid as it circulates back to the surface outside the drill shaft. The drilling fluid carrying the debris is often referred-to as "mud," "sludge," or "flowback."

Common materials found in the mud, sludge, or flowback are rock and sand, and a variety of hydrocarbons such as oil and petroleum present in the drilling fluid. The mud or sludge often has a high salt content dependent upon where the drilling takes place. The salt content of the drilling fluid may often be near or even higher than an average salinity found in the ocean (approximately 35 parts per thousand). Furthermore, the mud or sludge has been found to contain toxins and heavy metals which also contaminate the sludge.

The average drilling process can generate 300,000 barrels of mud, sludge, flowback per day over a two week period, or the equivalent of 4,200,000 barrels of mud or sludge for each drilled well. The mud, sludge, or flowback generated in drilling processes is typically shipped, temporarily stored, treated, and/or disposed of in an insertion well.

In some embodiments, the disclosed cellulase will be used as a high temperature viscosity breaker to enhance oil and gas operations. More specifically, the disclosed cellulase of the present invention will be applied to a fracturing fluid when hydraulic fracturing is performed in oil or gas wells.

The enzyme encoded by SEQ ID NO:1, as well as cellulases and amylases encoded by other polynucleotides disclosed herein, such as SEQ ID NO:5, SEQ ID NO:7, SEQ ID NO:9, SEQ ID NO:11, SEQ ID NO:13, and/or SEQ ID NO:15, or obtainable by methods disclosed herein, may potentially be used to hydrolyze a broad spectrum of polysaccharides—many of which are useful oil and gas drilling, fracturing and well clean-up operations. The disclosed cellulases exhibit broad spectrum $\beta$-glycosidase activity, e.g., against guar, hydroxypropyl guar, carboxymethyl guar, carboxymethyl hydroxypropyl guar, carboxymethyl cellulose, barley $\beta$-glucan, and locust bean gum. The enzyme activity pattern is preferably both endo and exo, allowing effective reduction in the viscosity of polysaccharides, e.g., guar and derivatized guar solutions, by cleaving within long polysaccharide chains and also by cleaving disaccharide units from the ends of the polymers. Besides the aforementioned polysaccharides, other substrates of the disclosed enzymes include those capable of forming linear or cross-linked gels. Examples of suitable polysaccharide substrates include glactomannan gums, guars, derivatized guars, cellulose and cellulose derivatives, starch, starch derivatives, xanthan, derivatized xanthan and mixtures thereof. Specific examples also include, but are not limited to, guar gum, guar gum derivative, locust bean gum, karaya gum, xanthan gum, cellulose and cellulose derivatives, etc. Typical polymers or gelling agents to which the disclosed enzymes may be directed include guar gum, hydroxypropyl guar, carboxymethyl hydroxypropyl guar, hydroxyethyl cellulose, carboxymethyl hydroxyethyl cellulose, carboxymethyl cellulose, dialkyl carboxymethyl cellulose, etc. Other examples of polymers include, but are not limited to, phosphomannans, scleroglucans, dextrans and other types of polymers. In some embodiments, a polymer substrate is carboxymethyl hydroxypropyl guar. In some embodiments, a disclosed enzyme may also be effective in hydrolyzing biogums (e.g., succinoglycan biogums made from date syrup or sucrose).

In some embodiments, a disclosed enzyme may be used to hydrolyze cellulose-containing or derivatized cellulose-containing polymers—typically, the enzymes attack glucosidic linkages of the cellulose backbone. The disclosed enzymes may be suitable for degrading the polymer into mostly monosaccharide units, in some cases, by specifically hydrolyzing the exo(1,4)-$\beta$-D-glucosidic and endo(1,4)-$\beta$-D-glucosidic linkages between monosaccharide units and the cellulose backbone in the (1,4)-$\beta$-D-glucosidic linkages of any cellobiose fragments.

In each fracturing job that uses the disclosed cellulases, field operators will generally first perform an enzyme dose optimization study in an industrial lab. Such studies may include dilution of the cellulase to a concentration of 10~400 ppm and mixed with linear or cross-linked guar gum (25-60 lb/1,000 gal). Depending on the application conditions, guar gum maybe cross-linked using a cross-linker, especially for wells where higher temperature, pressure, and pH conditions are present. The enzyme dose information resulting from such optimization studies may then be used in the actual fracturing job.

The unique activity of the disclosed cellulase allows for the hydrolysis of guar-based fracturing fluids in a smooth and controlled manner in deep wells, where high temperature and high pH conditions are present. Compared to chemical breakers, the disclosed cellulase of the present invention provides a non-corrosive and environmentally benign alternative to the harsh and non-selective chemical breakers.

In some embodiments of the present invention the cellulase may be used to treat, clean, or alter fluids used in oil and gas exploration activities. In a further aspect the cellulase of this invention will treat or alter the fluids, in part, or completely, so that the fluids may be used again, or recycled, for use in additional oil and gas exploration activities or to be disposed of in an environmentally friendly way.

The invention provides compositions and methods of using polysaccharide degrading enzymes to treat flowback from oil and gas exploration and drilling operations. In some aspects, the compositions and methods disclosed herein are used to degrade polysaccharides, which may include starch and or guar gum, present in flowback fluid, by adding polysaccharide-degrading enzymes to the flowback fluids.

In some embodiments, the enzymes used in the method are a cellulase, or an amylase, or a combination thereof to treat flowback produced by oil and gas exploration and drilling operations.

In some embodiments, the compositions disclosed herein, including amylases and cellulases, as described herein, are added to a flowback fluid. In some embodiments the compositions and methods disclosed herein include an environmental trigger step, (e.g. pH, salinity, or mechanical treatment system step) which activates the compositions disclosed herein, including the amylases and cellulases described herein.

The enzyme-comprising compositions disclosed herein can be formulated in a variety of forms, e.g., as liquids, gels, pills, tablets, sprays, powders, pellets or encapsulated forms, including nanoencapsulated forms.

Well Completion

The walls of oil and gas formations are exposed during the process of drilling a borehole. The successful completion of a well bore requires the deposit of a low-permeable filter cake on the walls of the well bore to seal the permeable formation exposed by the drilling bit. A filter cake can limit drilling fluid losses from the well bore and protect the natural formation from possible damage by the fluids permeating into the well bore. Solids in the flowback fluid may also damage the formation, particularly drilling fines. The suspension of fine particles that enters the formation while the cake is being established is known as "mud spurt" and the liquid that enters subsequently is known as "filtrate." For a filter cake to form, the drilling fluid must contain some particles of a size only slightly smaller than the pore openings of the formation. These particles are known as bridging particles and are trapped in surface pores, thereby forming a bridge over the formation pores. Filter cake building fluids can also contain polymers for suspension of solids and for reducing liquid loss through the filter cake by encapsulating the bridging particles. These can be either natural or synthetic polymers. The polymers can include one polymer such as xanthan selected for its rheological properties and a second polymer, a starch for example, selected for reduction of fluid loss. At completion of the drilling or other well servicing, the filter cake must be removed to allow production of the formation fluids or bonding of cement to the formation at the completion stage. Removal of the deposited filter cake should be as complete as possible to recover permeability within the formation. Typically, when the filter cake is removed from the well bore, or cleaned from the well bore, some of the polymers used to create the filter cake remain intact and are carried to the surface in the flowback fluid.

Hydraulic Fracturing

In a hydraulic fracturing process, aqueous fracturing fluid is injected under pressure into the bore hole. The pressure drives the fluid into cracks, fissures, and fractures in the formation, forcing such openings to become larger and propagate. Proppant material contained therein wedges into the expanded cracks, fissures and fractures to help hold them open when the pressure is reduced and to provide improved formation permeability. The injected fracturing fluid mixes with groundwater, gas, and other materials present in the subterranean environment.

When the pressure is removed, this fluid mixture flows back to the surface and gas is extracted therefrom. The fracturing fluid mixture after extraction is referred to as "flowback fluid," the recovered water and fracturing fluid which flow back from oil or gas well drilling fracturing operation. This flowback fluid typically can be anywhere from 10-60% percent of the volume of fluid that is injected into the well, and it flows back over a period of several days to several weeks or longer after fracturing. A significant amount of fracturing fluid can remain in the formation. At a certain point there is a transition between primarily recovering fracturing fluid to that of produced water. A typical fracturing job on a Marcellus shale formation could require 20,000 barrels to 150,000 barrels of fracturing fluid, depending upon the number of stages pumped. For a project pumping 40,000 barrels of fracturing fluid, the load recovery could be 50% or 20,000 barrels of flowback. After the initial several week post-fracturing recovery, an additional 10,000 to 30,000 barrels of flowback liquid may flow from the well for two years.

Flowback liquid may consist of water, the fracturing chemicals that were injected into the well, including but not limited to guar gum, proponent, and cross-linker, as well as any contaminants that are present in the rock formation water. In addition to natural salinity of water in the formation, any fresh water that is injected into the well during the fracturing process will tend to dissolve salts in the formation, thus increasing the salinity of the flowback liquid.

Treatment Systems

U.S. Pat. Nos. 4,536,293; 5,093,008; 6,132,619; 4,896,665; 6,110,382; 4,465,598; 7,754,080, all of which are hereby incorporated by reference in their respective entireties, disclose methods of treating flowback liquids from drilling and oil discovery processes. This method, and other filtration methods used to treat flowback fluids have the potential of becoming clogged. Flowback treatment systems, and/or filters, including but not limited to reverse osmosis filters, have the tendency to become clogged or inefficient in processing flowback fluid because of the viscosity and/or flow rate of the flowback fluid.

Treating Flowback Fluids

The invention provides methods using one or more enzymes or enzyme cocktails as described herein, wherein the method treats, or is a step in the treatment, of flowback fluids produced by drilling and exploration operations by degrading viscous, starch containing, or polysaccharide components of the flowback fluid. Thus, this method decreases the viscosity and/or flow rate of flowback fluids.

In some aspects, the invention provides for formulating an enzyme treatment (using an enzyme used to practice the invention) by blending together an aqueous fluid and a polypeptide used to practice the invention; adding the enzyme treatment to the flowback fluids; allowing the enzyme treatment to degrade the viscous polysaccharide-materials materials in the flowback fluid, wherein the enzyme treatment is effective to break down or hydrolyze the starch and/or polysaccharide components of such fluids.

In some embodiments, polypeptide used to practice the invention may be capable of breaking bonds within the recovered fluid or flowback. In some embodiments, the enzymes may be capable of reducing the viscosity or increasing the flow rate of the flowback fluids.

In some embodiments, polypeptide used to practice the invention will reduce the likelihood of clogging in systems used to treat flowback fluid.

In some embodiments polypeptide used to practice the invention will be added to a system or device used to treat flowback fluids. In some embodiments the polypeptide used to practice the invention will be added to the flowback fluid to enhance previously known flowback fluid treatments.

In some embodiments, the polypeptide used to practice the invention disclosed herein will be used in combination with microbes used to treat flowback fluid.

In some embodiments, the enzymes will be used to break down materials in the flowback fluid.

In a another embodiment, the enzymes will be used to break down filter cake materials or fracturing materials in the flowback fluid.

In some embodiments, polypeptide used to practice the invention described may be encapsulated to stabilize the enzyme, improve thermostability and alkaline pH tolerance, and provide controlled release. Examples of breaker encapsulation compositions and methods are provided in U.S. Pat. Nos. 5,164,099, 6,163,766, 5,373,901, 5,437,331, and 6,357,527, the disclosures of each of which are incorporated herein by reference thereto.

In some embodiments, polypeptide used to practice the invention is encapsulated, having a coating or membrane that hydrolytically degrades allowing better control of release time and ease of handling not previously afforded. For example, because the polypeptide used to practice the invention is encapsulated in a material that reacts with water, rather than simply dissolves or dissipates in water, the release can be controlled through the reaction rate of the coating with water. Likewise, by insulating the polypeptide used to practice the invention from the harsh conditions (high temperature and pH) for some period of time, can provide delayed degradation. Those skilled in the art will appreciate that the reaction rate of the coating (and therefore the breaker release profile) can be varied broadly depending on the encapsulating polymer chemistry employed.

In some embodiments, the disclosed enzymes such as cellulases and amylases are thermotolerant and/or thermostable; for example, the enzyme can retain at least 75% residual activity (e.g., glucanase activity) after 2 minutes at 95° C.; and in another aspect, retains 100% activity after heating for 30 minutes at 95° C. In yet another aspect, the enzyme retains 100% activity after heating for 30 minutes at 96° C., 97° C., 98° C. or 99° C. In yet another aspect, the disclosed cellulases retain at least 90% activity after heating for 30 minutes at 100° C.

In some embodiments, the cellulase enzymes described herein possess glucanase, e.g., endoglucanase, mannanase, xylanase activity or a combination of these activities. In some aspects, the glucanase activity is an endoglucanase activity (e.g., endo-1,4-beta-D-glucan 4-glucano hydrolase activity) and comprises hydrolysis of 1,4-beta-D-glycosidic linkages in cellulose, cellulose derivatives (e.g., carboxy methyl cellulose and hydroxy ethyl cellulose) lichenin, beta-1,4 bonds in mixed beta- 1,3 glucans, such as cereal beta-D-glucans or xyloglucans and other plant material containing cellulosic parts. In alternative aspects, these glucanases e.g., endoglucanases, mannanases, xylanases have increased activity and stability, including thermotolerance or thermostability, at increased or decreased pHs and temperatures.

Examples of suitable polysaccharide substrates of some of the enzymes disclosed herein include galactomannan gums, guars, derivatized guars, cellulose and cellulose derivatives, starch, starch derivatizes, xanthan, derivatized xanthan and mixtures thereof. Specific examples also include, but are not limited to, guar gum, guar gum derivative, locust bean gum, karaya gum, xanthan gum, cellulose and cellulose derivatives, etc. Typical polymeric viscosifiers or gelling agents to which the disclosed enzymes may be directed include guar gum, hydroxypropyl guar, carboxymethyl hydroxypropyl guar, hydroxyethyl cellulose, carboxymethyl hydroxyethyl cellulose, carboxymethyl cellulose, dialkyl carboxymethyl cellulose, etc. Other examples of polymers include, but are not limited to, phosphomannons, scerolglucons, dextrans and other types of polymers. In some embodiments, a polymer substrate is carboxymethyl hydroxypropyl guar. In some embodiments, a disclosed enzyme may also be effective in hydrolyzing biogums (e.g., succinoglycan biogums made from date syrup or sucrose). In some embodiments, a disclosed enzyme may be used to hydrolyze cellulose-containing or derivatized cellulose-containing polymers—typically, the enzymes attack glucosidic linkages of the cellulose backbone. The disclosed enzymes may be suitable for degrading the polymer into mostly monosaccharide units, in some cases, by specifically hydrolyzing the exo(1,4)-β-D-glucosidic and endo(1,4)-β-D-glucosidic linkages between monosaccharide units and the cellulose backbone in the (1,4)-β-D-glucosidic linkages of any cellobiose fragments.

DESCRIPTION OF THE FIGURES

FIG. 3 depicts a bar graph showing the level of activity of protein preparations, as described in Example 4.

FIG. 4 depicts SEQ ID NO:1, the polynucleotide with 14 silent mutations: T6C, T9C, T15G, A22C, G24T, A33C, A39C, A40C, A42C, A54C, A57C, T66C, G81A, A84C, as compared to SEQ ID NO:3.

FIG. 5 depicts SEQ ID NO:2, the polypeptide encoded by SEQ ID NO:1, 3, and 4.

FIG. 6 depicts SEQ ID NO:3, the unmodified parent polynucleotide sequence of SEQ ID NO:1 and 4.

FIG. 7 depicts SEQ ID NO:4, the polynucleotide with 14 silent mutations: T6C, T9C, T15G, A22C, G24T, A33C, A39C, A40C, A42C, A54C, A57C, T66C, G81A, A84C, as compared to SEQ ID NO:3, plus one additional point mutation upstream from the start codon (additional upstream sequence shown).

FIG. 8 depicts the nucleic acid of SEQ ID NO:5.
FIG. 9 depicts the polypeptide of SEQ ID NO:6.
FIG. 10 depicts the nucleic acid of SEQ ID NO:7.
FIG. 11 depicts the polypeptide of SEQ ID NO:8.
FIG. 12 depicts the nucleic acid of SEQ ID NO:9.
FIG. 13 depicts the polypeptide of SEQ ID NO:10.
FIG. 14 depicts the nucleic acid of SEQ ID NO:11.
FIG. 15 depicts the polypeptide of SEQ ID NO:12.
FIG. 16 depicts the nucleic acid of SEQ ID NO:13.
FIG. 17 depicts the polypeptide of SEQ ID NO:14.

FIG. 18 depicts the nucleic acid of SEQ ID NO:15.
FIG. 19 depicts the polypeptide of SEQ ID NO:16.

DEFINITION OF TERMS

"cellulase" refers to enzymes having cellulase, endoglucanase, cellobiohydrolase, beta-glucosidase, xylanase, mannanase, β-xylosidase, arabinofuranosidase, and/or oligomerase activity.

"cellulolytic activity" is an enzyme having cellulase, endoglucanase, cellobiohydrolase, beta-glucosidase, xylanase, mannanase, β-xylosidase, arabinofuranosidase, and/or oligomerase activity.

A "codon" is a three polynucleotide sequence that specifies the identity of an amino acid to be added to a protein.

A "silent mutation" is a mutation in a codon that does not result in the specification of a different amino acid.

An "Open Reading Frame" is a series of codons that specifies the sequence of amino acids in a protein.

A base "position" is the numerical location of a base in a polynucleotide sequence, counted consecutively from the start of the open reading frame or from some other reference marker.

To "encode" a protein means to specify the amino acid sequence of that protein.

A "mutation" is a change in a nucleotide sequence or an amino acid sequence compared to a reference.

A "nucleotide" refers to one of the four bases which comprise DNA sequence—Adenine (A), Thymidine (T), Guanidine (G), and Cytosine (C).

"*Thermotoga maritima* genomic sequence" refers to the *Thermotoga maritima* strain MSB8 genomic sequence specified by GenBank Accession No. AE000512.

An "Expression level" for a given protein is the amount of protein generated by an expression system, such as a transformed cell culture as measured per unit volume of cell culture.

An "Expression level" for a given enzyme is the amount of enzyme activity generated by an expression system, such as a transformed cell culture as measured per unit volume of cell culture.

"Wild-type" refers to a protein or nucleic acid sequence that can be obtained in nature.

EXAMPLE 1

Use of SEQ ID NO. 2 with Ester

Figure 1:
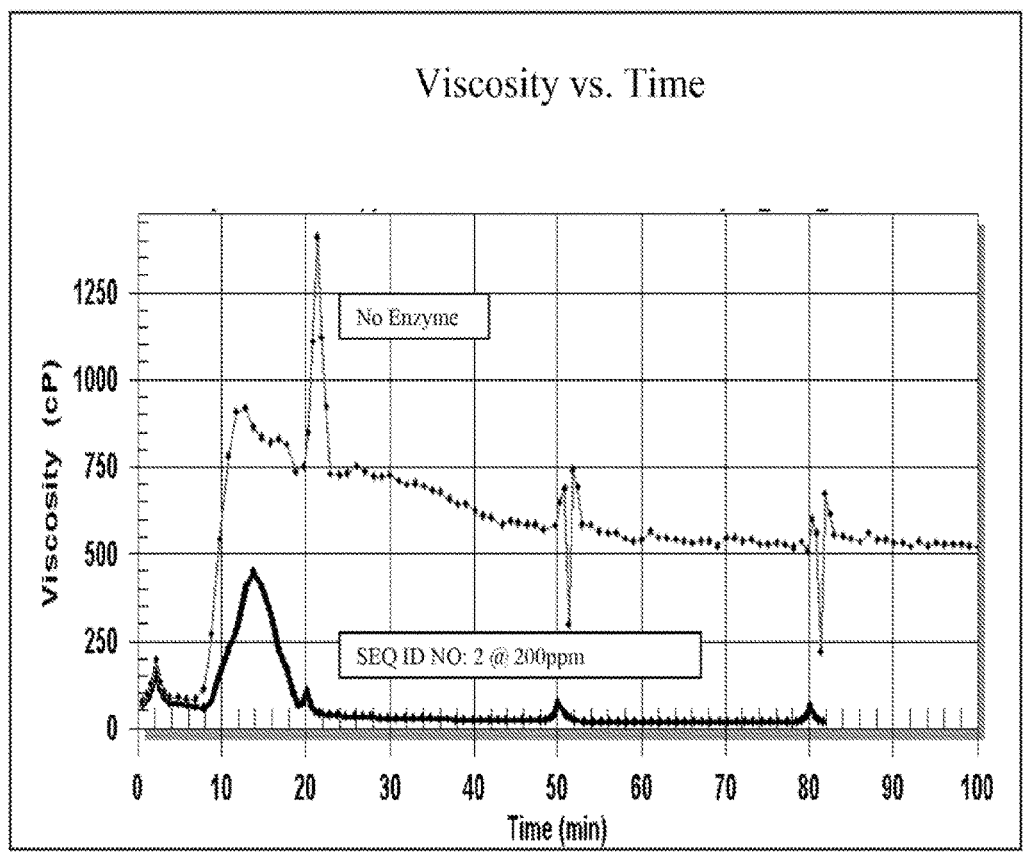
FIG. 1 depicts an image of a rheology graph displaying the viscometery of two guar solutions against time, as described in Example 1.

Rheology testing was performed using a Grace M5600 HPHT Rheometer, two samples were assayed, one with the cellulase encoded by SEQ ID NO. 2, and the other, a control, with no enzyme. The assay conditions were as follows: sample 1, included the cellulase encoded by SEQ ID NO. 2 at 200 ppm, 0.25 pptg ester, 25 pptg cross-linked guar, at pH 10.5, at 180 degrees Fahrenheit; sample 2, included 0.25 pptg ester, 25 pptg cross-linked guar, at pH 10.5, at 180 degrees Fahrenheit. As displayed in FIG. 1, the sample including cellulase encoded by SEQ ID NO. 2 and ester at pH 10.5, and 180 degrees Fahrenheit (bottom line) reached nearly 0 centipoise (cP), whereas the control sample with no enzyme maintained a viscosity of 500 cP (top line).

Example 2

Method of Making Enhanced Expression Variants

Two variants (SEQ ID NO:1 and NO: 4) were designed based on SEQ ID NO:3 to mutate at the DNA level to improve the gene expression. The design takes into account of many factors that may influence gene expression. The mutations were introduced on the PCR primers using PCR techniques known of those of skill in the art. Both genes were PCR-amplified and cloned into the *Pseudomonas* vector pDOW 1169 (DOW AgroSciences, IN) using standard molecular cloning techniques. The resulting expression constructs were transformed into *Pseudomonas fluorescens* DC454 (DOW AgroSciences, IN). A transformant with the SEQ ID NO:1 was designated as the lead as it showed the most enhanced expression.

EXAMPLE 3

Using SDS-PAGE Gel Electrophoresis and Nonspecific Protein Staining to Visualize Expression Levels of the SEQ ID NO:2 Polypeptide Expressed by Constructs Comprising SEQ ID NOs:1, 3, and 4

Criterion™ precast Tris-HCl polyacrylamide gel (Bio-rad Laboratories, Inc.) was used to separate proteins. The gel was run at 150V using Tris-glycine buffer (see FIG. 1). Protein loading was normalized to load proteins from 0.33 $OD_{600}$ cells for each lane. SeeBlue® pre-stained protein standard was used (Life Technologies). The gel was stained with a nonspecific dye, and each lane was visually inspected for the presence of a band at the size of SEQ ID NO:2, about 37 kilodaltons.

The results indicate that there is a single band having an accumulation level which varies across samples and which is absent from the negative control. This band has a size expected for SEQ ID NO:2.

The accumulation level of this band is significantly higher in lanes corresponding to protein extracts from cells harboring constructs comprising SEQ ID NO:1, and to a lesser extend SEQ ID NO:4, that SEQ ID NO:3 or the negative control.

EXAMPLE 4

Method of Determining Relative Expression Levels for Variants

Figure 2:
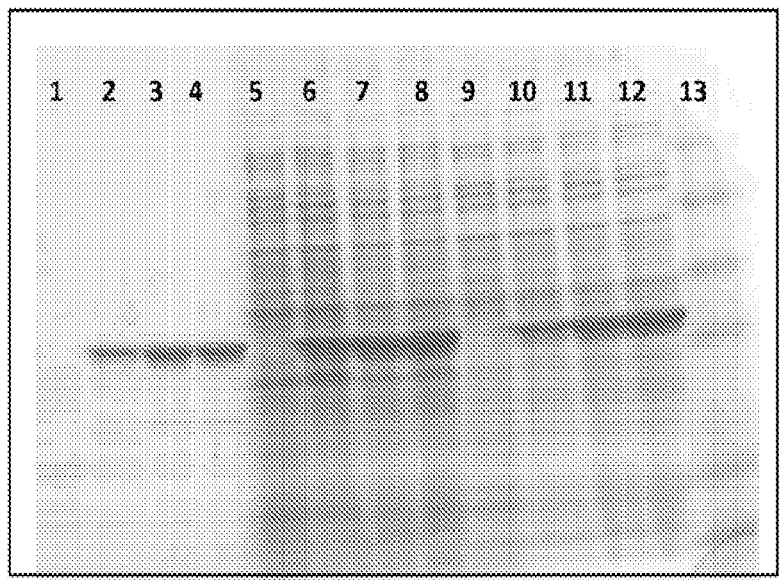
FIG. 2 depicts an image of SDS PAGE gel electrophoresis displaying various level of protein expression, as described in Example 3.

Nucleic acid sequence comprising SEQ ID NO:1, SEQ ID NO:3 and SEQ ID NO:4 gene were transformed into a suitable host cell for expression of the protein of SEQ ID NO:2. The cells were cultured in flasks so that the encoded protein would be expressed. The cultures were grown at 30° C. and 220 rpm to an OD600 of ~0.9 in a designed complex medium, and induced with 0.3 mM IPTG (Isopropyl β-D-1-thiogalactopyranoside) for 24 hours. Cells were harvested and lysed either by sonication or heat-treatment at 80° C. for 1 hour. Cellulase activity was measured by a p-Nitrophenyl (pNP) based assay using pNP-□-D-lactopyroanoside as substrate. (Advances in Carbohydrate Chemistry and Biochemistry, Academic Press, 1999). Activity levels were measured in U/ml as shown in FIG. 2 to determine relative expression levels from each culture.

The results indicate that cells harboring the construct comprising SEQ ID NO:1 demonstrated significantly more SEQ ID NO:2 activity than those harboring SEQ ID NO:4, and that both SEQ ID NOs:1 and 4 yielded a greater amount of activity of the expressed protein than the cells harboring SEQ ID NO:3.

What is claimed is:

1. An isolated, recombinant, or synthetic nucleic acid molecule comprising a nucleotide sequence selected from the group consisting of:
   (a) the nucleotide sequence of SEQ ID NO: 1; and
   (b) a nucleotide sequence having at least 90% sequence identity to the nucleotide sequence of SEQ ID NO: 3 with at least five mutations selected from A54C, A57C, T66C, G81A, A84C, A6C, G6C, A9C, G9C, A15G, C15G, T22C, G22C, A24T, C24T, T33C, G33C, T39C, G39C, T40C, G40C, T42C, G42C, T54C, G54C, T57C, G57C, A66C, G66C, C81A, T81A, T84C, G84C, and any combination thereof,
   wherein said nucleic acid molecule encodes a polypeptide having cellulase activity.

2. The isolated, recombinant, or synthetic nucleic acid molecule of claim 1, wherein at least one of said mutations is silent.

3. The isolated, recombinant, or synthetic nucleic acid molecule of claim 1, wherein at least one of said mutations directs expression of a cellulase from said sequence at a higher level than a reference nucleotide sequence lacking said at least one mutation.

4. The isolated, recombinant, or synthetic nucleic acid molecule of claim 1, wherein said nucleotide sequence encodes the polypeptide set forth in the amino acid sequence of SEQ ID NO: 2 and, wherein said nucleotide sequence has been mutated with respect to a reference nucleotide sequence encoding the polypeptide set forth in the amino acid sequence of SEQ ID NO: 2 such that the expression level of said polypeptide by said mutated nucleotide sequence is increased relative to the expression level of said polypeptide encoded by said reference nucleotide sequence.

5. An isolated, recombinant, or synthetic nucleic acid molecule encoding a polypeptide comprising an amino acid sequence that has at least 90%, 95%, 97%, 98%, 99% or 100% sequence identity to the amino acid sequence of SEQ ID NO: 2 with at least five mutations corresponding to nucleotides at positions of the nucleotide sequence of SEQ ID NO: 1 selected from the group consisting of T6C, T9C, T15G, A22C, G24T, A33C, A39C, A40C, A42, A54C, A57C, T66C, G81A, A84C, A6C, G6C, A9C, G9C, A15G, C15G, T22C, G22C, A24T, C24T, T33C, G33C, T39C, G39C, T40C, G40C, T42C, G42C, T54C, G54C, T57C, G57C, A66C, G66C, C81A, T81A, T84C, G84C, and any combination thereof, wherein said nucleic acid molecule encodes a polypeptide having cellulase activity.

6. An isolated, recombinant, or synthetic nucleic acid molecule comprising a nucleotide sequence having at least 90% sequence identity to the nucleotide sequence of SEQ ID NO: 3 with at least two mutations selected from the group consisting of: T9C, T15G, A22C, G24T, A33C, A40C, A42C, A54C, A57C, T66C, G81A, A9C, G9C, A15G, C15G, T22C, G22C, A24T, C24T, T33C, G33C, T40C, G40C, T42C, G42C, T54C, G54C, T57C, G57C, A66C, G66C, C81A, T81A, and any combination thereof, wherein said nucleic acid molecule encodes a polypeptide having cellulase activity.

7. A bacterial expression system comprising the isolated, recombinant, or synthetic nucleic acid molecule of claim 1, 5, or 6.

8. The bacterial expression system of claim 7, wherein a cellulase encoded by said nucleic acid molecule is produced in said bacterial expression system at an amount that is at least 1.0 g/L, 2.0 g/L, 3.0 g/L, 4.0 g/L, 5.0 g/L, 6.0 g/L, 7.0 g/L, 8.0 g/L, 9.0 g/L, 10.0 g/L, 11.0 g/L, 12.0 g/L, 13.0 g/L, 14.0 g/L, 15.0 g/L, 16.0 g/L, 17.0 g/L, 18.0 g/L, 19.0 g/L, 20.0 g/L, 21.0 g/L, 22.0 g/L, 23.0 g/L, 24.0 g/L, 25.0, g/L, 26.0 g/L, 27.0 g/L, 28.0 g/L, 29.0 g/L, 30.0 g/L, 31.0 g/L, 32.0 g/L, 33.0 g/L, 34.0 g/L, or 35.0 g/L.

9. The bacterial expression system of claim 7, wherein said bacterial expression system is a gram-negative bacterial expression system.

10. The gram-negative bacterial expression system of claim 9, wherein said gram-negative bacterial expression system is a *Pseudomonas, E. coli, Ralstonia*, or *Caulobacter* expression system.

11. The gram-negative bacterial expression system of claim 10, wherein said gram-negative bacterial expression system is a recombinant *Pseudomonas fluorescens* expression system.

12. The isolated, recombinant, or synthetic nucleic acid molecule of claim 6, wherein at least one of said mutations is silent.

13. The isolated, recombinant, or synthetic nucleic acid molecule of claim 6, wherein at least one of said mutations directs expression of a cellulase from said sequence at a higher level than a reference nucleotide sequence lacking said at least one mutation.

14. The isolated, recombinant, or synthetic nucleic acid molecule of claim 6, wherein said nucleotide sequence encodes the polypeptide set forth in the amino acid sequence of SEQ ID NO: 2 and, wherein said nucleotide sequence has been mutated with respect to a reference nucleotide sequence encoding the polypeptide set forth in the amino acid sequence of SEQ ID NO: 2 such that the expression level of said polypeptide by said mutated nucleotide sequence is increased relative to the expression level of said polypeptide encoded by said reference nucleotide sequence.

* * * * *

SEQUENCE LISTING

<160> NUMBER OF SEQ ID NOS: 16

<210> SEQ ID NO 1
<211> LENGTH: 954
<212> TYPE: DNA
<213> ORGANISM: Artificial Sequence
<220> FEATURE:
<223> OTHER INFORMATION: Open reading frame encoding SEQ ID NO:2
      conveying enhanced protein expression

<400> SEQUENCE: 1

```
atgggcgtcg atccgtttga acgtaacaaa atcttgggcc gcggcattaa tatcggcaat      60
gcgctcgaag caccaaatga aggcgactgg ggagtggtga taaagatgaa gttcttcgac     120
attataaaag aagccggttt ctctcatgtt cgaattccaa taagatggag tacgcacgct     180
caggcgtttc ctccttataa aatcgagcct tctttcttca aaagagtgga tgaagtgata     240
aacggagccc tgaaaagagg actggctgtt gttataaata ttcatcacta cgaggagtta     300
atgaatgatc cagaagaaca caaggaaaga tttcttgctc tttggaaaca aattgctgat     360
cgttataaag actatcccga aactctattt tttgaaattc tgaatgaacc tcacggaaat     420
cttactccgg aaaaatggaa tgaactgctt gaggaagctc taaaagttat aagatcaatt     480
gacaaaaagc acactgtgat tataggcaca gctgaatggg ggggtatatc tgcccttgaa     540
aaactgaggg tcccaaaatg ggaaaaaaat gcgatagtta caattcacta ctacaatcct     600
ttcgaattta cccatcaagg agctgagtgg gtgcctggat ctgagaaatg gttgggaaga     660
aagtggggat ctccagatga tcagaaacat ttgatagaag aattcaattt tatagaagaa     720
tggtcaaaaa agaacaaaag accaatttac ataggtgagt ttggtgccta cagaaaagct     780
gaccttgaat caagaataaa atggacctcc tttgtcgttc gcgaagccga gaaaggggg     840 tggagctggg catactggga attttgttcc ggttttggtg tttatgatcc tctgagaaaa     900
cagtggaata aagatctttt agaagcttta ataggaggag atagcattga atga           954
```

<210> SEQ ID NO 2
<211> LENGTH: 317
<212> TYPE: PRT
<213> ORGANISM: Thermotoga maritima - Cellulase

<400> SEQUENCE: 2

```
Met Gly Val Asp Pro Phe Glu Arg Asn Lys Ile Leu Gly Arg Gly Ile
  1               5                  10                  15

Asn Ile Gly Asn Ala Leu Glu Ala Pro Asn Glu Gly Asp Trp Gly Val
             20                  25                  30

Val Ile Lys Asp Glu Phe Phe Asp Ile Ile Lys Glu Ala Gly Phe Ser
         35                  40                  45

His Val Arg Ile Pro Ile Arg Trp Ser Thr His Ala Gln Ala Phe Pro
     50                  55                  60

Pro Tyr Lys Ile Glu Pro Ser Phe Phe Lys Arg Val Asp Glu Val Ile
 65                  70                  75                  80

Asn Gly Ala Leu Lys Arg Gly Leu Ala Val Val Ile Asn Ile His His
             85                  90                  95

Tyr Glu Glu Leu Met Asn Asp Pro Glu His Lys Glu Arg Phe Leu
            100                 105                 110

Ala Leu Trp Lys Gln Ile Ala Asp Arg Tyr Lys Asp Tyr Pro Glu Thr
        115                 120                 125

Leu Phe Phe Glu Ile Leu Asn Glu Pro His Gly Asn Leu Thr Pro Glu
    130                 135                 140
```

Lys Trp Asn Glu Leu Leu Glu Glu Ala Leu Lys Val Ile Arg Ser Ile
145                 150                 155                 160

Asp Lys Lys His Thr Val Ile Ile Gly Thr Ala Glu Trp Gly Gly Ile
            165                 170                 175

Ser Ala Leu Glu Lys Leu Arg Val Pro Lys Trp Glu Lys Asn Ala Ile
        180                 185                 190

Val Thr Ile His Tyr Tyr Asn Pro Phe Glu Phe Thr His Gln Gly Ala
    195                 200                 205

Glu Trp Val Pro Gly Ser Glu Lys Trp Leu Gly Arg Lys Trp Gly Ser
210                 215                 220

Pro Asp Asp Gln Lys His Leu Ile Glu Glu Phe Asn Phe Ile Glu Glu
225                 230                 235                 240

Trp Ser Lys Lys Asn Lys Arg Pro Ile Tyr Ile Gly Glu Phe Gly Ala
            245                 250                 255

Tyr Arg Lys Ala Asp Leu Glu Ser Arg Ile Lys Trp Thr Ser Phe Val
        260                 265                 270

Val Arg Glu Ala Glu Lys Arg Gly Trp Ser Trp Ala Tyr Trp Glu Phe
    275                 280                 285

Cys Ser Gly Phe Gly Val Tyr Asp Pro Leu Arg Lys Gln Trp Asn Lys
290                 295                 300

Asp Leu Leu Glu Ala Leu Ile Gly Gly Asp Ser Ile Glu
305                 310                 315

<210> SEQ ID NO 3
<211> LENGTH: 954
<212> TYPE: DNA
<213> ORGANISM: Thermotoga maritima

<400> SEQUENCE: 3
atgggtgttg atccttttga aggaacaaa atattgggaa gaggcattaa tataggaaat    60
gcgcttgaag caccaaatga gggagactgg ggagtggtga taaaagatga gttcttcgac   120
attataaaag aagccggttt ctctcatgtt cgaattccaa taagatggag tacgcacgct   180
caggcgtttc ctccttataa aatcgagcct tctttcttca aaagagtgga tgaagtgata   240
aacggagccc tgaaaagagg actggctgtt gttataaata ttcatcacta cgaggagtta   300
atgaatgatc cagaagaaca caaggaaaga tttcttgctc tttggaaaca aattgctgat   360
cgttataaag actatcccga aactctattt tttgaaattc tgaatgaacc tcacggaaat   420
cttactccgg aaaaatggaa tgaactgctt gaggaagctc taaaagttat aagatcaatt   480
gacaaaaagc acactgtgat tataggcaca gctgaatggg ggggtatatc tgcccttgaa   540
aaactgaggg tcccaaaatg gaaaaaaat gcgatagtta caattcacta ctacaatcct   600
ttcgaattta cccatcaagg agctgagtgg gtgcctggat ctgagaaatg gttgggaaga   660
aagtggggat ctccagatga tcagaaacat ttgatagaag aattcaattt tatagaagaa   720
tggtcaaaaa agaacaaaag accaatttac ataggtgagt ttggtgccta cagaaaagct   780
gaccttgaat caagaataaa atggacctcc tttgtcgttc gcgaagccga gaaagggggg   840
tggagctggg catactggga attttgttcc ggttttggtg tttatgatcc tctgagaaaa   900
cagtggaata agatcttttt agaagcttta ataggaggag atagcattga ataa           954

<210> SEQ ID NO 4
<211> LENGTH: 976
<212> TYPE: DNA
<213> ORGANISM: Artificial Sequence

```
<220> FEATURE:
<223> OTHER INFORMATION: 5' region and open reading frame encoding SEQ
      ID NO:2 having modest increased expression

<400> SEQUENCE: 4
tctactagtt aggaggtaac ttatgggcgt cgatccgttt gaacgtaaca aaatcttggg      60
ccgcggcatt aatatcggca atgcgctcga agcaccaaat gaaggcgact ggggagtggt     120
gataaaagat gagttcttcg acattataaa agaagccggt ttctctcatg ttcgaattcc     180
aataagatgg agtacgcacg ctcaggcgtt tcctccttat aaaatcgagc cttctttctt     240
caaaagagtg gatgaagtga taacggagcc cctgaaaaga ggactggctg ttgttataaa     300
tattcatcac tacgaggagt taatgaatga tccagaagaa cacaaggaaa gatttcttgc     360
tctttggaaa caaattgctg atcgttataa agactatccc gaaactctat tttttgaaat     420
tctgaatgaa cctcacggaa atcttactcc ggaaaaatgg aatgaactgc ttgaggaagc     480
tctaaaagtt ataagatcaa ttgacaaaaa gcacactgtg attataggca gctgaatg     540
gggggggtata tctgcccttg aaaaactgag ggtcccaaaa tgggaaaaaa atgcgatagt     600
tacaattcac tactacaatc ctttcgaatt tacccatcaa ggagctgagt gggtgcctgg     660
atctgagaaa tggttgggaa gaaagtgggg atctccagat gatcagaaac atttgataga     720
agaattcaat tttatagaag aatggtcaaa aagaacaaaa gaccaattt acataggtga     780
gtttggtgcc tacagaaaag ctgaccttga atcaagaata aaatggacct cctttgtcgt     840
tcgcgaagcc gagaaagggg ggtggagctg gcatactgga aattttgtt ccggttttgg     900
tgtttatgat cctctgagaa aacagtggaa taaagatctt tagaagctt aataggagg     960
agatagcatt gaatga                                                    976

<210> SEQ ID NO 5
<211> LENGTH: 954
<212> TYPE: DNA
<213> ORGANISM: Artificial Sequence
<220> FEATURE:
<223> OTHER INFORMATION: Open reading frame encoding cellulase

<400> SEQUENCE: 5
atgggtgttg atccttttga aaggaacaaa atattgggaa gaggcattaa tataggaaat      60
gcgcttgaag caccaaatga gggagactgg ggagtggtga taaagatga gttcttcgac     120
attataaaag aagccggttt ctctcatgtt cgaattccaa taagatggag tacgcacgct     180
tacgcgtttc ctccttataa aatcatggat cgcttcttca aaagagtgga tgaagtgata     240
aacggagccc tgaaaagagg actggctgtt gttataaata ttcatcacta cgaggagtta     300
atgaatgatc cagaagaaca aggaaagat tttcttgctc tttggaaaca aattgctgat     360
cgttataaag actatcccga aactctattt tttgaaattc tgaatgaacc tcacggaaat     420
cttactccgg aaaaatggaa tgaactgctt gaggaagctc taaaagttat aagatcaatt     480
gacaaaaagc acactataat tataggcaca gctgaatggg gggtatatc tgcccttgaa     540
aaactgtctg tcccaaaatg gaaaaaaat tctatagtta caattcacta ctacaatcct     600
ttcgaattta cccatcaagg agctgagtgg gtggaaggat ctgagaaatg gttgggaaga     660
aagtggggat ctccagatga tcagaaacat tgatagaag aattcaattt tatagaagaa     720
tggtcaaaaa gaacaaaag accaattac ataggtgagt ttggtgccta cagaaaagct     780
gaccttgaat caagaataaa atggacctcc tttgtcgttc gcgaaatgga gaaaggaga     840
tggagctggg catactggga attttgttcc ggttttggtg tttatgatac tctgagaaaa     900
```
acctggaata aagatctttt agaagcttta ataggaggag atagcattga ataa 954

<210> SEQ ID NO 6
<211> LENGTH: 317
<212> TYPE: PRT
<213> ORGANISM: Cellulase

<400> SEQUENCE: 6

```
Met Gly Val Asp Pro Phe Glu Arg Asn Lys Ile Leu Gly Arg Gly Ile
  1               5                  10                  15

Asn Ile Gly Asn Ala Leu Glu Ala Pro Asn Glu Gly Asp Trp Gly Val
             20                  25                  30

Val Ile Lys Asp Glu Phe Phe Asp Ile Ile Lys Glu Ala Gly Phe Ser
         35                  40                  45

His Val Arg Ile Pro Ile Arg Trp Ser Thr His Ala Tyr Ala Phe Pro
     50                  55                  60

Pro Tyr Lys Ile Met Asp Arg Phe Phe Lys Arg Val Asp Glu Val Ile
 65                  70                  75                  80

Asn Gly Ala Leu Lys Arg Gly Leu Ala Val Val Ile Asn Ile His His
                 85                  90                  95

Tyr Glu Glu Leu Met Asn Asp Pro Glu His Lys Glu Arg Phe Leu
            100                 105                 110

Ala Leu Trp Lys Gln Ile Ala Asp Arg Tyr Lys Asp Tyr Pro Glu Thr
            115                 120                 125

Leu Phe Phe Glu Ile Leu Asn Glu Pro His Gly Asn Leu Thr Pro Glu
        130                 135                 140

Lys Trp Asn Glu Leu Leu Glu Glu Ala Leu Lys Val Ile Arg Ser Ile
145                 150                 155                 160

Asp Lys Lys His Thr Ile Ile Gly Thr Ala Glu Trp Gly Gly Ile
                165                 170                 175

Ser Ala Leu Glu Lys Leu Ser Val Pro Lys Trp Glu Lys Asn Ser Ile
            180                 185                 190

Val Thr Ile His Tyr Tyr Asn Pro Phe Glu Phe Thr His Gln Gly Ala
        195                 200                 205

Glu Trp Val Glu Gly Ser Glu Lys Trp Leu Gly Arg Lys Trp Gly Ser
    210                 215                 220

Pro Asp Asp Gln Lys His Leu Ile Glu Glu Phe Asn Phe Ile Glu Glu
225                 230                 235                 240

Trp Ser Lys Lys Asn Lys Arg Pro Ile Tyr Ile Gly Glu Phe Gly Ala
                245                 250                 255

Tyr Arg Lys Ala Asp Leu Glu Ser Arg Ile Lys Trp Thr Ser Phe Val
            260                 265                 270

Val Arg Glu Met Glu Lys Arg Arg Trp Ser Trp Ala Tyr Trp Glu Phe
        275                 280                 285

Cys Ser Gly Phe Gly Val Tyr Asp Thr Leu Arg Lys Thr Trp Asn Lys
    290                 295                 300

Asp Leu Leu Glu Ala Leu Ile Gly Gly Asp Ser Ile Glu
305                 310                 315
```

<210> SEQ ID NO 7
<211> LENGTH: 972
<212> TYPE: DNA
<213> ORGANISM: Artificial Sequence
<220> FEATURE:
<223> OTHER INFORMATION: Open reading frame encoding cellulase

<400> SEQUENCE: 7

```
atggaacagt cagttgctga aagtgatagc aactcagcat ttgaatacaa caaaatggta    60
ggtaaaggag taaatattgg aaatgcttta gaagctcctt tcgaaggagc ttggggagta   120
agaattgagg atgaatattt tgagataata agaaaaggg gatttgattc tgttaggatt   180
cccataagat ggtcagcaca tatatccgaa aagccaccat atgatattga caggaatttc   240
ctcgaaagag ttaaccatgt tgtcgatagg gctcttgaga taaatttaac agtaatcatc   300
aatacgcacc attttgaaga actctatcaa gaaccggata aatacggcga tgttttggtg   360
gaaatttgga gacagattgc aaaattcttt aaagattacc cggaaaatct gttctttgaa   420
atctacaacg agcctgctca gaacttgaca gctgaaaaat ggaacgcact ttatccaaaa   480
gtgctcaaag ttatcaggga gagcaatcca acccggattg tcattatcga tgctccaaac   540
tgggcacact atagcgcagt gagaagtcta aaattagtca cgacaaacg catcattgtt   600
tccttccatt actacgaacc tttcaaattc acacatcagg gtgccgaatg ggttaatccc   660
atcccacctg ttagggttaa gtggaatggc gaggaatggg aaattaacca atcagaagt   720
catttcaaat acgtgagtga ctgggcaaag caaataacg taccaatctt tcttggtgaa   780
ttcggtgctt attcaaaagc agacatggac tcaagggtta gtggaccga agtgtgaga   840
aaaatggcgg aagaatttgg attttcatac gcgtattggg aattttgtgc aggatttggc   900
atatacgata gatggtctca aaactggatc gaaccattgg caacagctgt ggttggcaca   960
ggcaaagagt aa                                                       972
```

<210> SEQ ID NO 8
<211> LENGTH: 323
<212> TYPE: PRT
<213> ORGANISM: Cellulase

<400> SEQUENCE: 8

```
Met Glu Gln Ser Val Ala Glu Ser Asp Ser Asn Ser Ala Phe Glu Tyr
  1               5                  10                  15
Asn Lys Met Val Gly Lys Gly Val Asn Ile Gly Asn Ala Leu Glu Ala
             20                  25                  30
Pro Phe Glu Gly Ala Trp Gly Val Arg Ile Glu Asp Glu Tyr Phe Glu
         35                  40                  45
Ile Ile Lys Lys Arg Gly Phe Asp Ser Val Arg Ile Pro Ile Arg Trp
     50                  55                  60
Ser Ala His Ile Ser Glu Lys Pro Pro Tyr Asp Ile Asp Arg Asn Phe
 65                  70                  75                  80
Leu Glu Arg Val Asn His Val Val Asp Arg Ala Leu Glu Asn Asn Leu
                 85                  90                  95
Thr Val Ile Ile Asn Thr His His Phe Glu Glu Leu Tyr Gln Glu Pro
            100                 105                 110
Asp Lys Tyr Gly Asp Val Leu Val Glu Ile Trp Arg Gln Ile Ala Lys
        115                 120                 125
Phe Phe Lys Asp Tyr Pro Glu Asn Leu Phe Phe Glu Ile Tyr Asn Glu
    130                 135                 140
Pro Ala Gln Asn Leu Thr Ala Glu Lys Trp Asn Ala Leu Tyr Pro Lys
145                 150                 155                 160
Val Leu Lys Val Ile Arg Glu Ser Asn Pro Thr Arg Ile Val Ile Ile
                165                 170                 175
Asp Ala Pro Asn Trp Ala His Tyr Ser Ala Val Arg Ser Leu Lys Leu
            180                 185                 190
```

Val Asn Asp Lys Arg Ile Ile Val Ser Phe His Tyr Tyr Glu Pro Phe
    195                 200                 205

Lys Phe Thr His Gln Gly Ala Glu Trp Val Asn Pro Ile Pro Pro Val
    210                 215                 220

Arg Val Lys Trp Asn Gly Glu Glu Trp Glu Ile Asn Gln Ile Arg Ser
225                 230                 235                 240

His Phe Lys Tyr Val Ser Asp Trp Ala Lys Gln Asn Asn Val Pro Ile
                245                 250                 255

Phe Leu Gly Glu Phe Gly Ala Tyr Ser Lys Ala Asp Met Asp Ser Arg
            260                 265                 270

Val Lys Trp Thr Glu Ser Val Arg Lys Met Ala Glu Gly Phe Gly Phe
        275                 280                 285

Ser Tyr Ala Tyr Trp Glu Phe Cys Ala Gly Phe Gly Ile Tyr Asp Arg
    290                 295                 300

Trp Ser Gln Asn Trp Ile Glu Pro Leu Ala Thr Ala Val Val Gly Thr
305                 310                 315                 320

Gly Lys Glu

<210> SEQ ID NO 9
<211> LENGTH: 974
<212> TYPE: DNA
<213> ORGANISM: Artificial Sequence
<220> FEATURE:
<223> OTHER INFORMATION: Cellulase 7xGene site saturation mutagenesis
      product and 3' sequence

<400> SEQUENCE: 9
atgggtgttg atccttttga aggaacaaa atattgggaa gaggcattaa tataggaaat      60
gcgcttgaag caccaaatga gggagactgg ggagtggtga taaaagatga gtatttcgac    120
attataaaag aagccggttt ctctcatgtt cgaattccaa taagatggag tacgcacgct    180
caggcgtttc ctccttataa aatcgaggat cgcttcttca aaagagtgga tgaagtgata    240
aacggagccc tgaaaagagg actggctgtt gttataaatc agcatcacta cgaggagtta    300
atgaatgatc cagaagaaca caaggaaaga tttcttgctc tttggaaaca aattgctgat    360
cgttataaag actatcccga aactctattt tttgaaattc tgaatgaacc tcacggaaat    420
cttactccgg aaaaatggaa tgaactgctt gaggaagctc taaagttat aagatcaatt    480 gacaaaaagc acactataat tataggcaca gctgaatggg ggggtatatc tgcccttgaa    540
aaactgaggg tcccaaaatg ggaaaaaaat gcgatagtta caattcacta ctacaatcct    600
ttcgaattta cccatcaagg agctgagtgg gtggaaggat ctgagaaatg gttgggaaga    660
aagtggggat ctccagatga tcagaaacat tgatagaag aattcaattt tatagaagaa    720
tggtcaaaaa agaacaaaag accaatttac ataggtgagt ttggtgccta cagaaaagct    780
gaccttgaat caagaataaa atggacctcc tttgtcgttc gcgaagctga aaaggaga    840 tggagctggg catactggga attttgttcc ggttttggtg tttatgatac tctgagaaaa    900
acctggaata aagatctttt agaagcttta ataggaggag atagcattga ataacaccat    960
tccaagatgg cgtg                                                     974

<210> SEQ ID NO 10
<211> LENGTH: 323
<212> TYPE: PRT
<213> ORGANISM: Cellulase

<400> SEQUENCE: 10

Met Gly Val Asp Pro Phe Glu Arg Asn Lys Ile Leu Gly Arg Gly Ile
1               5                   10                  15

Asn Ile Gly Asn Ala Leu Glu Ala Pro Asn Glu Gly Asp Trp Gly Val
            20                  25                  30

Val Ile Lys Asp Glu Tyr Phe Asp Ile Ile Lys Glu Ala Gly Phe Ser
        35                  40                  45

His Val Arg Ile Pro Ile Arg Trp Ser Thr His Ala Gln Ala Phe Pro
    50                  55                  60

Pro Tyr Lys Ile Glu Asp Arg Phe Phe Lys Arg Val Asp Glu Val Ile
65              70                  75                  80

Asn Gly Ala Leu Lys Arg Gly Leu Ala Val Val Ile Asn Gln His His
                85                  90                  95

Tyr Glu Glu Leu Met Asn Asp Pro Glu His Lys Glu Arg Phe Leu
                100                 105                 110

Ala Leu Trp Lys Gln Ile Ala Asp Arg Tyr Lys Asp Tyr Pro Glu Thr
        115                 120                 125

Leu Phe Phe Glu Ile Leu Asn Glu Pro His Gly Asn Leu Thr Pro Glu
    130                 135                 140

Lys Trp Asn Glu Leu Leu Glu Glu Ala Leu Lys Val Ile Arg Ser Ile
145                 150                 155                 160

Asp Lys Lys His Thr Ile Ile Gly Thr Ala Glu Trp Gly Gly Ile
                165                 170                 175

Ser Ala Leu Glu Lys Leu Arg Val Pro Lys Trp Glu Lys Asn Ala Ile
            180                 185                 190

Val Thr Ile His Tyr Tyr Asn Pro Phe Glu Phe Thr His Gln Gly Ala
        195                 200                 205

Glu Trp Val Gly Ser Glu Lys Trp Leu Gly Arg Lys Trp Gly Ser
    210                 215                 220

Pro Asp Asp Gln Lys His Leu Ile Glu Glu Phe Asn Phe Ile Glu Glu
225             230                 235                 240

Trp Ser Lys Lys Asn Lys Arg Pro Ile Tyr Ile Gly Glu Phe Gly Ala
                245                 250                 255

Tyr Arg Lys Ala Asp Leu Glu Ser Arg Ile Lys Trp Thr Ser Phe Val
        260                 265                 270

Val Arg Glu Ala Glu Lys Arg Arg Trp Ser Trp Ala Tyr Trp Glu Phe
    275                 280                 285

Cys Ser Gly Phe Gly Val Tyr Asp Thr Leu Arg Lys Thr Trp Asn Lys
    290                 295                 300

Asp Leu Leu Glu Ala Leu Ile Gly Gly Asp Ser Ile Glu His His Ser
305                 310                 315                 320

Lys Met Ala

<210> SEQ ID NO 11
<211> LENGTH: 954
<212> TYPE: DNA
<213> ORGANISM: Artificial Sequence
<220> FEATURE:
<223> OTHER INFORMATION: Cellulase 31x-1 7xGene site saturation
      mutagenesis product

<400> SEQUENCE: 11
atgggtgttg atccttttga aaggaacaaa atattgggaa gaggcattaa tataggaaat      60
gcgcttgaag caccaaatga gggagactgg ggagtggtga taaaagatga gtatttcgac     120
attataaaag aagccggttt ctctcatgtt cgaattccaa taagatggag tacgcacgct     180

```
caggcgtttc ctccttataa aatcgaggat tctttcttca aaagagtgga tgaagtgata    240
aacggagccc tgaaaagagg actggctgtt gttataaata ttcatcacta cgaggagtta    300
atgaatgatc cagaagaaca caaggaaaga tttcttgctc tttggaaaca aattgctgat    360
cgttataaag actatcccga aactctattt tttgaaattc tgaatgaacc tcacggaaat    420
cttactccgg aaaaatggaa tgaactgctt gaggaagctc taaaagttat aagatcaatt    480
gacaaaaagc acactgtgat tataggcaca gctgaatggg ggggtatatc tgcccttgaa    540
aaactgaggg tcccaaaatg ggaaaaaaat gcgatagtta caattcacta ctacaatcct    600
ttcgaattta cccatcaagg agctgagtgg gtgcctggat ctgagaaatg gttgggaaga    660
aagtggggat ctccagatga tcagaaacat gtgatagaag aattcaattt tatagaagaa    720
tggtcaaaaa agaacaaaag accaatttac ataggtgagt tggtgcctta cagaaaagct    780
gaccttgaat caagaataaa atggacctcc tttgtcgttc gcgaagccga gaaaggggg    840 tggagctggg catactggga attttgttcc ggttttggtg tttatgatcc tctgagaaaa    900
cagtggaata aagatctttt agaagctcta ataggaggag atagcattga ataa    954
```

<210> SEQ ID NO 12
<211> LENGTH: 317
<212> TYPE: PRT
<213> ORGANISM: Cellulase

<400> SEQUENCE: 12

```
Met Gly Val Asp Pro Phe Glu Arg Asn Lys Ile Leu Gly Arg Gly Ile
  1               5                  10                  15

Asn Ile Gly Asn Ala Leu Glu Ala Pro Asn Glu Gly Asp Trp Gly Val
             20                  25                  30

Val Ile Lys Asp Glu Tyr Phe Asp Ile Ile Lys Glu Ala Gly Phe Ser
         35                  40                  45

His Val Arg Ile Pro Ile Arg Trp Ser Thr His Ala Gln Ala Phe Pro
     50                  55                  60

Pro Tyr Lys Ile Glu Asp Ser Phe Phe Lys Arg Val Asp Glu Val Ile
 65                  70                  75                  80

Asn Gly Ala Leu Lys Arg Gly Leu Ala Val Val Ile Asn Ile His His
                 85                  90                  95

Tyr Glu Glu Leu Met Asn Asp Pro Glu Glu His Lys Glu Arg Phe Leu
            100                 105                 110

Ala Leu Trp Lys Gln Ile Ala Asp Arg Tyr Lys Asp Tyr Pro Glu Thr
        115                 120                 125

Leu Phe Phe Glu Ile Leu Asn Glu Pro His Gly Asn Leu Thr Pro Glu
    130                 135                 140

Lys Trp Asn Glu Leu Leu Glu Glu Ala Leu Lys Val Ile Arg Ser Ile
145                 150                 155                 160

Asp Lys Lys His Thr Val Ile Ile Gly Thr Ala Glu Trp Gly Gly Ile
                165                 170                 175

Ser Ala Leu Glu Lys Leu Arg Val Pro Lys Trp Glu Lys Asn Ala Ile
            180                 185                 190

Val Thr Ile His Tyr Tyr Asn Pro Phe Glu Phe Thr His Gln Gly Ala
        195                 200                 205

Glu Trp Val Pro Gly Ser Glu Lys Trp Leu Gly Arg Lys Trp Gly Ser
    210                 215                 220

Pro Asp Asp Gln Lys His Val Ile Glu Glu Phe Asn Phe Ile Glu Glu
225                 230                 235                 240
```

Trp Ser Lys Lys Asn Lys Arg Pro Ile Tyr Ile Gly Glu Phe Gly Ala
            245                 250                 255

Tyr Arg Lys Ala Asp Leu Glu Ser Arg Ile Lys Trp Thr Ser Phe Val
        260                 265                 270

Val Arg Glu Ala Glu Lys Arg Gly Trp Ser Trp Ala Tyr Trp Glu Phe
    275                 280                 285

Cys Ser Gly Phe Gly Val Tyr Asp Pro Leu Arg Lys Gln Trp Asn Lys
290                 295                 300

Asp Leu Leu Glu Ala Leu Ile Gly Gly Asp Ser Ile Glu
305                 310                 315

<210> SEQ ID NO 13
<211> LENGTH: 954
<212> TYPE: DNA
<213> ORGANISM: Artificial Sequence
<220> FEATURE:
<223> OTHER INFORMATION: Cellulase 12X-1 combined Gene site saturation
      mutagenesis product

<400> SEQUENCE: 13
atgggtgttg atcctttga aggaacaaa atattgggaa gaggcattaa tataggaaat      60
gcgcttgaag caccaaatga gggagactgg ggagtggtga taaagatga gttcttcgac     120 attataaaag aagccggttt ctctcatgtt cgaattccaa taagatggag tacgcacgct    180
caggcgtttc ctccttataa aatcgaggat tctttcttca aaagagtgga tgaagtgata    240
aacggagccc tgaaaagagg actggctgtt gttataaatc agcatcacta cgaggagtta    300
atgaatgatc agaagaaca caaggaaaga tttcttgctc tttggaaaca aattgctgat    360
cgttataaag actatcccga aactctattt tttgaaattc tgaatgaacc tcacggaaat    420
cttactccgg aaaaatggaa tgaactgctt gaggaagctc taaaagttat aagatcaatt    480
gacaaaaagc acactgtgat tataggcaca gctgaatggg ggggtatatc tgcccttgaa    540
aaactgaggg tcccaaaatg ggaaaaaaat gcgatagtta caattcacta ctacaatcct    600
ttcgaattta cccatcaagg agctgagtgg gtgcctggat ctgagaaatg gttgggaaga    660
aagtggggat ctccagatga tcagaaacat ttgatagaag aattcaattt tatagaagaa    720
tggtcaaaaa agaacaaaag accaatttac ataggtgagt ttggtgccta cagaaaagct    780
gaccttgaat caagaataaa atggaccttc ttgtcgttc gcgaagccga gaaaggggg      840 tggagctggg catactggga attttgttcc ggttttggtg tttatgatcc tctgagaaaa    900
cagtggaata aagatctttt agaagcttta ataggaggag atagcattga ataa          954

<210> SEQ ID NO 14
<211> LENGTH: 317
<212> TYPE: PRT
<213> ORGANISM: Cellulase

<400> SEQUENCE: 14

Met Gly Val Asp Pro Phe Glu Arg Asn Lys Ile Leu Gly Arg Gly Ile
1               5                   10                  15

Asn Ile Gly Asn Ala Leu Glu Ala Pro Asn Glu Gly Asp Trp Gly Val
            20                  25                  30

Val Ile Lys Asp Glu Phe Phe Asp Ile Ile Lys Glu Ala Gly Phe Ser
        35                  40                  45

His Val Arg Ile Pro Ile Arg Trp Ser Thr His Ala Gln Ala Phe Pro
    50                  55                  60

```
Pro Tyr Lys Ile Glu Asp Ser Phe Phe Lys Arg Val Asp Glu Val Ile
 65                  70                  75                  80

Asn Gly Ala Leu Lys Arg Gly Leu Ala Val Val Ile Asn Gln His His
                 85                  90                  95

Tyr Glu Glu Leu Met Asn Asp Pro Glu His Lys Glu Arg Phe Leu
            100                 105                 110

Ala Leu Trp Lys Gln Ile Ala Asp Arg Tyr Lys Asp Tyr Pro Glu Thr
            115                 120                 125

Leu Phe Phe Glu Ile Leu Asn Glu Pro His Gly Asn Leu Thr Pro Glu
            130                 135                 140

Lys Trp Asn Glu Leu Leu Glu Glu Ala Leu Lys Val Ile Arg Ser Ile
145                 150                 155                 160

Asp Lys Lys His Thr Val Ile Ile Gly Thr Ala Glu Trp Gly Gly Ile
                165                 170                 175

Ser Ala Leu Glu Lys Leu Arg Val Pro Lys Trp Glu Lys Asn Ala Ile
            180                 185                 190

Val Thr Ile His Tyr Tyr Asn Pro Phe Glu Phe Thr His Gln Gly Ala
            195                 200                 205

Glu Trp Val Pro Gly Ser Glu Lys Trp Leu Gly Arg Lys Trp Gly Ser
        210                 215                 220

Pro Asp Asp Gln Lys His Leu Ile Glu Glu Phe Asn Phe Ile Glu Glu
225                 230                 235                 240

Trp Ser Lys Lys Asn Lys Arg Pro Ile Tyr Ile Gly Glu Phe Gly Ala
                245                 250                 255

Tyr Arg Lys Ala Asp Leu Glu Ser Arg Ile Lys Trp Thr Ser Phe Val
            260                 265                 270

Val Arg Glu Ala Glu Lys Arg Gly Trp Ser Trp Ala Tyr Trp Glu Phe
        275                 280                 285

Cys Ser Gly Phe Gly Val Tyr Asp Pro Leu Arg Lys Gln Trp Asn Lys
        290                 295                 300

Asp Leu Leu Glu Ala Leu Ile Gly Gly Asp Ser Ile Glu
305                 310                 315

<210> SEQ ID NO 15
<211> LENGTH: 1310
<212> TYPE: DNA
<213> ORGANISM: Artificial Sequence
<220> FEATURE:
<223> OTHER INFORMATION: Open reading frame encoding SEQ ID NO:16
      Amylase

<400> SEQUENCE: 15
atggccaagt actccgagct ggaaaagggc ggggtcataa tgcaggcgtt ctactgggac     60
gtgccttcag gaggaatatg gtgggacaca atacggcaga agataccgga gtggtacgat    120
gccggaatct ccgcaatatg gattcccccg gcgagcaagg gcatgggcgg cgcctattcg    180
atgggctacg accctacga cttctttgac ctcgtgagta cgaccagaag gaacggtag     240 agacgcgctt ggctccaag caggagctcg tgaacatgat aaacaccgcc cacgcctatg    300
gcatgaaggt aatagccgat atagtcatca accaccgcgc cggcggtgac ctggagtgga    360
accccttcgt gaacgactat acctggaccg acttctcaaa ggtcgcgtcg gtaaataca    420 cggccaacta cctcgacttc cacccgaacg agctccatgc gggcgattcc gggacatttg    480
gaggctatcc cgacatatgc cacgacaaga gctgggacca gtactggctc tgggccagcc    540
aggagagcta cgcggcatat ctcaggagca tcggcatcga tgcctggcgc ttcgactacg    600
```

| | |
|---|---|
| tcaagggcta tgctccctgg gtcgtcaagg actggctgaa ctggtgggga ggctgggcgg | 660 |
| ttggagagta ctgggacacc aacgtcgacg ctgttctcaa ctgggcatac tcgagcggtg | 720 |
| ccaaggtctt tgacttcgcc ctctactaca agatggatga ggcctttgac aacaaaaaca | 780 |
| ttccagcgct cgtctctgcc cttcagaacg ccagactgt tgtctcccgc gacccgttca | 840 |
| aggccgtaac ctttgtagca aaccacgaca ccgatataat ctggaacaag tatccagcct | 900 |
| acgcgttcat cctcacctac gagggccagc cgacaatatt ctaccgcgac tacgaggagt | 960 |
| ggctcaacaa ggataagctc aagaacctca tctggataca tgagaacctc gccggaggaa | 1020 |
| gcaccgacat agtctactac gataacgatg aactcatctt cgtcaggaac ggctacgggg | 1080 |
| acaagccggg gcttataacc tacatcaacc taggctcgag caaggccgga aggtgggttt | 1140 |
| atgtgccgaa gttcgcgggc gcgtgcatcc acgagtatac tggtaacctc ggaggctggg | 1200 |
| tagacaagta cgtctactca agcggctggg tctatctcga agctccagct tacgaccctg | 1260 |
| ccaacgggca gtatggctac tccgtgtgga gctactgcgg ggtgggctga | 1310 |

<210> SEQ ID NO 16
<211> LENGTH: 436
<212> TYPE: PRT
<213> ORGANISM: Amylase

<400> SEQUENCE: 16

Met Ala Lys Tyr Ser Glu Leu Glu Lys Gly Gly Val Ile Met Gln Ala
1               5                   10                  15

Phe Tyr Trp Asp Val Pro Ser Gly Gly Ile Trp Trp Asp Thr Ile Arg
            20                  25                  30

Gln Lys Ile Pro Glu Trp Tyr Asp Ala Gly Ile Ser Ala Ile Trp Ile
        35                  40                  45

Pro Pro Ala Ser Lys Gly Met Gly Gly Ala Tyr Ser Met Gly Tyr Asp
    50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Met Lys Val Ile Ala Asp Ile Val Ile Asn His
            100                 105                 110

Arg Ala Gly Gly Asp Leu Glu Trp Asn Pro Phe Val Asn Asp Tyr Thr
        115                 120                 125

Trp Thr Asp Phe Ser Lys Val Ala Ser Gly Lys Tyr Thr Ala Asn Tyr
    130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Ala Pro Trp Val
        195                 200                 205

Val Lys Asp Trp Leu Asn Trp Trp Gly Gly Trp Ala Val Gly Glu Tyr
    210                 215                 220

Trp Asp Thr Asn Val Asp Ala Val Leu Asn Trp Ala Tyr Ser Ser Gly
225                 230                 235                 240

Ala Lys Val Phe Asp Phe Ala Leu Tyr Tyr Lys Met Asp Glu Ala Phe
                245                 250                 255

```
                    Asp Asn Lys Asn Ile Pro Ala Leu Val Ser Ala Leu Gln Asn Gly Gln
                                260                 265                 270

Thr Val Val Ser Arg Asp Pro Phe Lys Ala Val Thr Phe Val Ala Asn
                                275                 280                 285

His Asp Thr Asp Ile Ile Trp Asn Lys Tyr Pro Ala Tyr Ala Phe Ile
                        290                 295                 300

Leu Thr Tyr Glu Gly Gln Pro Thr Ile Phe Tyr Arg Asp Tyr Glu Glu
                    305                 310                 315                 320

Trp Leu Asn Lys Asp Lys Leu Lys Asn Leu Ile Trp Ile His Glu Asn
                                325                 330                 335

Leu Ala Gly Gly Ser Thr Asp Ile Val Tyr Tyr Asp Asn Asp Glu Leu
                                340                 345                 350

Ile Phe Val Arg Asn Gly Tyr Gly Asp Lys Pro Gly Leu Ile Thr Tyr
                                355                 360                 365

Ile Asn Leu Gly Ser Ser Lys Ala Gly Arg Trp Val Tyr Val Pro Lys
                        370                 375                 380

Phe Ala Gly Ala Cys Ile His Glu Tyr Thr Gly Asn Leu Gly Gly Trp
                    385                 390                 395                 400

Val Asp Lys Tyr Val Tyr Ser Ser Gly Trp Val Tyr Leu Glu Ala Pro
                                405                 410                 415

Ala Tyr Asp Pro Ala Asn Gly Gln Tyr Gly Tyr Ser Val Trp Ser Tyr
                                420                 425                 430

Cys Gly Val Gly
                                435
```